United States Patent

Dunn et al.

[11] Patent Number: 6,019,965
[45] Date of Patent: Feb. 1, 2000

[54] METHODS FOR TREATMENT OF PULMONARY DISEASE USING GM-CSF

[75] Inventors: Ashley Roger Dunn, Parkville, Australia; Edouard Guy Stanley, London, United Kingdom; Graham John Lieschke, Parkville, Australia; Dianne Grail, Parkville, Australia; Kerry J. Fowler, Parkville, Australia

[73] Assignee: Ludwig Institute for Cancer Research, New York, N.Y.

[21] Appl. No.: 09/044,960

[22] Filed: Mar. 20, 1998

Related U.S. Application Data

[62] Division of application No. 08/211,651, Oct. 24, 1994, Pat. No. 5,777,193.

[51] Int. Cl.⁷ ............................. A61K 38/19; A61K 9/12
[52] U.S. Cl. .................................. 424/85.1; 514/2; 514/8; 514/12; 514/885
[58] Field of Search .................. 514/2, 8, 12, 885; 424/85.1

[56] References Cited

U.S. PATENT DOCUMENTS 5,162,111  11/1992  Grabstein et al. ............. 424/85.1
5,545,536  8/1996  Kaushansky et al. ............. 435/69.1

OTHER PUBLICATIONS

E. Stanley et al., *The EMBO Journal,* 4:2569–2573 (1985).

M. Tsuchiya et al., *Eur. J. Biochem.,* 165:7–12 (1987).

S.L. Mansour et la., *Nature,* 336:349–352 (1988).

H. Tushida et al., *Nature,* 345:442–444 (1990).

H. Schorle et al., *Nature,* 352:621–624 (1991).

A. Bradley et al., *Biotechnology,* 10:534–539 (1992).

G. Dranuff et al., *Science,* 264;713–716 (1994).

J.A. Huffman et al., *J. Clin. Invest.,* 97:649–655 (1996).

Lieschke et al., *Clinical Oncology Society of Australia Inc.,* Annual Scientific Meeting. Abstract only.

Stedman's Medical Dictionary, 24th Ed. p. 1272.

*Primary Examiner*—Prema Mertz
*Attorney, Agent, or Firm*—Fulbright & Jaworski, LLP

[57] ABSTRACT

Methods of treatment of pulmonary disease, e.g., alveolar proteinosis, by treating a subject with an effective amount of GM-CSF.

5 Claims, 13 Drawing Sheets

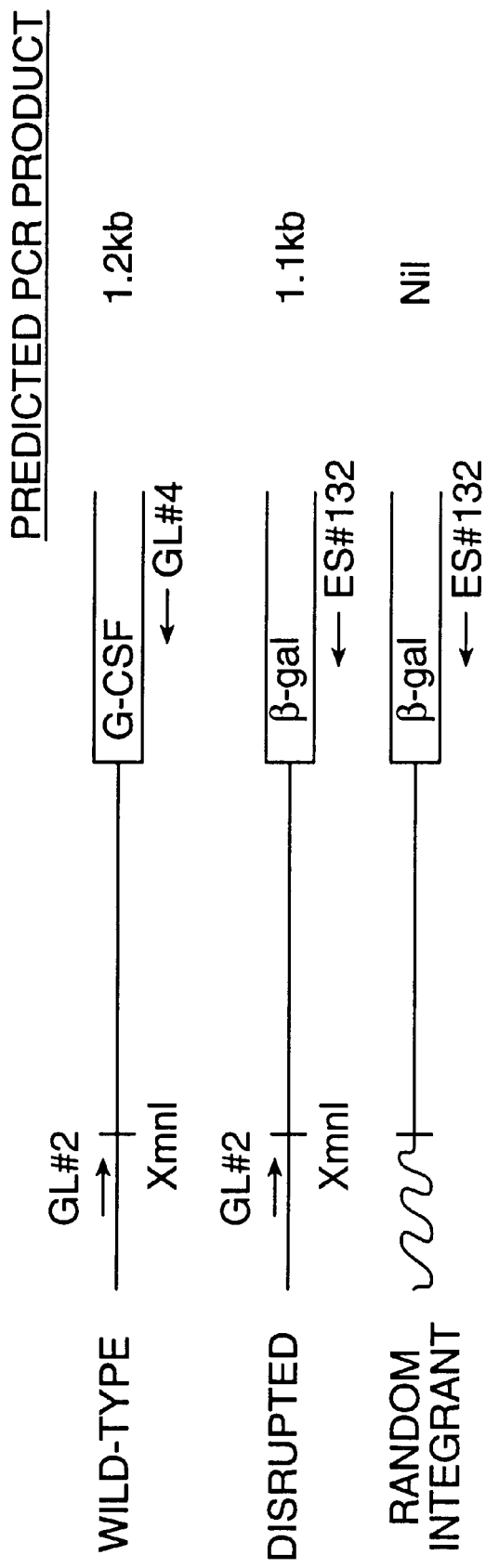

FIRST LITTER FROM G-CSF chimera (=+/-) x +/- MATING

FIG. 10 GERMLINE TRANSMISSION OF G-CSF KNOCK-OUT MUTATION
PCR analysis of tail DNA from chimeras and their progeny

METHODS FOR TREATMENT OF PULMONARY DISEASE USING GM-CSF

This application is a divisional application of 08/211,651 filed Oct. 24, 1994 now U.S. Pat. No. 5,777,193.

This invention relates to animals having specifically designed alterations in pre-existing endogenous genetic loci, eg. animals having targeted disruptions of specific genes. In particular, the invention relates to animals in which the gene for a colony-stimulating factor is disrupted so as to create a null allele, whereby the animal does not express any detectable colony-stimulating factor. The colony-stimulating factor is granulocyte-macrophage colony-stimulating factor or granulocyte colony-stimulating factor. In a preferred embodiment of the invention, the animal is a rodent such as a mouse.

BACKGROUND OF THE INVENTION

Granulocyte-macrophage colony-stimulating factor (GM-CSF) is a haematopoietic growth factor which in vitro stimulates the survival, proliferation, differentiation and function of myeloid cells and their precursors, particularly neutrophil and eosinophil granulocytes and monocytel/macrophages (for review, see 1). The in vivo effects of GM-CSF have been studied in murine models by infecting pharmacological doses of GM-CSF (2), by generating GM-CSF tranagenic mice (3), and by reconstituting lethally irradiated mice with bone marrow cells overproducing GM-CSF (4).

These studies confirm the haematopoietic activity of GM-CSF in vivo, and suggest that excess levels of GM-CSF may be implicated in some disease processes. However, the usual physiological role of GM-CSF is not well defined (5). Endogenously-produced GM-CSF is not usually detectable in serum (6), and in humans altered serum levels have not correlated clearly with haematological or disease processes (1,6). It has been suggested that GM-CSF may be produced and act locally (1), but the cells producing G-CSF in vivo have yet to be identified. Moreover, it is not clear whether GM-CSF is an essential regulator for steady-state production of granulocytes and macrophages, or whether it is required as a regulator for emergency haematopoiesis in response to challenges such as bacterial infection. It is also not known whether GM-CSF is involved in the normal development of non-haematopoietic tissues.

Granulocyte colony-stimulating factor (G-CSF) is a haematopoietic growth factor which i vitro controls granulopoiesis. It stimulates the survival, proliferation, differentiation and function primarily of neutrophil granulocytes. As in the case of GM-CSF, the in vivo effects of G-CSF have been studied in murine models by injection of pharmacological doses of G-CSF, by generation of GM-CSF transgenic mice, and by reconstitution of lethally irradiated mice with bone marrow cells transformed with a retroviral vector carrying cDNA encoding G-CSF (reviewed in Reference 7). However, as with GM-CSF, the usual physiological role in vivo of G-CSF is unclear. It may act as a regulator in steady-state granulopoiesis, or may function as a regulator for emergency granulopoiesis in response to specific challenges requiring increased neutrophil production, such as infection (7).

G-CSF and its isolation, characterisation, and recombinant production have been extensively reviewed, for example papers cited in Reference 1.

Until recently, genetic studies depended upon the discovery of random mutations (either spontaneous or induced) or of pre-existing genetic polymorphisms. However, following the rapid development of recombinant DNA technology and of identification of specific genes, particularly in mice, by analogy to genes from other species or from the biochemistry of the protein products which they encode, methods for specifically-targeted deletion or modification of genes have been developed. Provided that a cloned, genomic fragment of the chosen genetic locus is available, it is possible to generate null alleles by disruption of the gene, to modify functional properties of the gene such as transcriptional pattern, mRNA or protein maturation pattern, or to modify the ability of the protein to interact with other gene products. This is achieved by using conventional recombinant DNA methods to introduce the desired mutation into a cloned DNA sequence of the chosen gene; the mutation is then transferred by means of homologous recombination into the genome of a pluripotent embryonic stem cell (ES cell). The ES cells thus produced are transferred by microinjection into mouse blastocysts in order to generate germ-line chimeras. Animals homozygous for the desired mutation are then generated by interbreeding of heterozygous siblings.

These techniques are now widely used, and have been employed to generate lineages of mice in which a variety of genes are disrupted; these mice are often referred to as "knock-out" mice. Many of these mutations are lethal, causing death early in embryonic life or in the perinatal period. The technique has been most successful in producing "knock-out" mice in which genes for molecules of immunological importance or for growth factors are deleted. The techniques are well established, and a variety of marker genes and genes employed to assist in selection of cells which have undergone homologous recombination rather than random integration of DNA are available. A number of reviews have been published [7 to 11], and techniques for generation of transgenic mice in general are reviewed in International Patent Application No. WO 91/13150 by Ludwig Institute for Cancer Research.

While such gene targeting is useful in the production of mouse models for genetically-determined human diseases, which models can be used for testing potential therapies, and while the techniques are well established in principle, it is not possible to predict in advance whether an animal line bearing a given targeted gene disruption can be generated, or if so how readily practicable generation of such a model will be and the best experimental approach to utilise. In particular, the frequency of transformation of the ES cells varies widely, from as little as 1 in 40,000 to as much as 1 in 150. While some of the factors involved in optimisation of transformation frequency are known, success is not easy to predict.

We have generated GM-CSF deficient and G-CSF deficient mice through targeted disruption of the GM-CSF and G-CSF genes respectively in embryonic stem cells. We have surprisingly found that while GM-CSF deficient mice have no major perturbation of haematopoiesis, they all have abnormal lungs and are prone to lung infections, implicating GM-CSF as being essential for normal pulmonary physiology and resistance to local infection. GM-CSF deficient mice are useful as a model system for the syndrome of alveolar proteinosis, and are particularly useful as a model system for the study of opportunistic infections and infections which are intractable to currently available therapies.

G-CSF deficient mice are neutropaenic, but have normal levels of monocytes/macrophages in the periphery. They are prone to sub-clinical infections, and will be useful in testing the efficacy of anti-microbial agents, especially in settings of increased vulnerability. They will also be useful in assessing the virulence of microorganisms.

SUMMARY OF THE INVENTION

According to one aspect of the invention, there is provided a non-human animal carrying a disruption of a gene encoding a colony stimulating factor.

Preferably the animal is a rodent, for example a mouse, rat, rabbit or hamster, and more preferably is a mouse.

In one preferred embodiment, this aspect of the invention provides a non-human animal carrying a disruption of the gene encoding granulocyte-macrophage colony-stimulating-factor (GM-CSF), such that expression of GM-CSF is disrupted. Preferably the spleen cells from the animal are incapable of producing detectable levels of bioactive GM-CSF.

Also preferably the-gene encoding GM-CSF is completely inactivated. Most preferably the animal carries a mutation comprising deletion of exons 1 and 2 and intron 1 between ScaI and SmaI restriction sites of the gene encoding GM-CSF.

In an alternative embodiment, this aspect of the invention provides a non-human animal carrying a disruption of the gene encoding granulocyte colony-stimulating factor (G-CSF), such that expression of the colony-stimulating factor is disrupted. Preferably the lung cells from the animal are incapable of producing detectable levels of bioactive G-CSF. Also preferably the gene encoding G-CSF is completely inactivated. Most preferably the animal carries a mutation comprising a deletion from the NcoI restriction site in exon 1 to the BamHI restriction site 6.3 kb 3' of the BamHI site in exon 3 of the gene encoding G-CSF.

Optionally the animals may also carry one or more additional mutations which result in disruption of a specific gene. For example, a GM-CSF deficient animal may also carry a mutation resulting in disruption of the gene for G-CSF, or vice versa. Again the animal in preferably a mouse, and the additional gene disruption may alternatively be targeted to a gene encoding a growth factor selected from the group consisting of colony-stimulating-factor-1 (CSF-1); leukaemia inhibitory factor (LIF), and transforming growth factor-β1(TGF-β1), or a cytokine, preferably an interleukin, including, but not limited to, an interleukin selected from the group consisting of interleukin-2, interleukin-3 and interleukin-6. Such double or multiple knock-out animals can be generated by crossing of animals in which the gene encoding GM-CSF or G-CSF is disrupted with animals in which the other desired gene(s) is disrupted. For example, the osteopetrotic mouse, a line which originated by spontaneous mutation, is known to be deficient in CSF-1, and has decreased levels of monocytes/macrophages and of osteoclasts. Preferably the animal is a mouse deficient in both GM-CSF and G-CSF, in GM-CSF and CSF-1, or in both G-CSF and CSF-1.

Cell lines, such as bone marrow stromal cell lines, derived from the novel animals described herein are also within the scope of this invention.

According to a second aspect, the novel animals of the invention, especially mice, provide a convenient model system for the study of disease. In one embodiment, this aspect of the invention provides a model system for the syndrome of alveolar proteinosis, both of the congenital form and the adult form, in which potential methods for treatment of this condition can be tested.

In an alternative embodiment, this aspect of the invention provides a model system for the study of infectious diseases, especially bacterial infections of the lungs. In particular, this model system is useful for the study of opportunistic infections of the type to which immunocompromised or immunodeficient individuals are prone, and also of infections which are intractable to currently-available therapies, including antibiotic treatment. Immunocompromised individuals include persons suffering from cancer, especially those undergoing chemotherapy and/or radiotherapy, persons suffering from leukaemias, transplant recipients undergoing immunosuppressive therapy, and persons with autoimmune diseases undergoing immunosuppressive therapy. A particularly important group of individuals prone to opportunistic infections are those suffering from acquired immunodeficiency syndrome (AIDS).

The animals of the invention are expected to be useful for the study not only of bacterial and viral infections, but also infections with fungi and mycoplasma. organisms suitable for study in the model system of the invention include, but are not limited to, Listeria, including *Listeria monocytogenes*, Mycobacteria, including *Mycobacterium tuberculosis, Mycobacterium intracellulare, Mycobacterium avium, Mycobacterium bovis* and atypical Mycobacteria; Pseudomonas species, including *Pseudomonas aeruginosa*, Enterobacteriaceae, including *Escherichia coli*, Salmonella species, Klebsiella species, including *Klebsiella pneumoniae* and *Klebsiella oxytoca; Pneumocystis carinii*; Histoplasma, including *Histoplasma capsulatum*; Cryptococcus, including *Cryptococcus neoformans*; Pasteurella, including *Pasteurella pestis* and *Pasteurella pseudotuberculosis* (now known as Yersinia pestis and *Yersinia pseudotuberculosis* respectively), and *Pasteurella multocida* (also known as *Pasteurella septica*); and Mycoplasma, including *Mycoplasma pneumoniae*.

According to a third aspect of the invention, there is provided a method of treatment of pulmonary infection comprising the step of administering to a subject in need of such treatment an effective amount of GM-CSF or of G-CSF. Preferably the GM-CSF or G-CSF can be administered locally to the lung. This may be achieved by means of aerosols or nebulisers, for example ultrasonically nebulised formulations. Suitable carriers and excipients are known in the art. In intensive care situations, the CSF may be administered via an endotracheal tube. Optionally the GM-CSF or G-CSF may be administered as adjunctive therapy, for example concurrently with other known treatments for the particular condition. This aspect of the invention also provides a method of treatment of alveolar proteinosis or of pulmonary infection, comprising the step of administering to a subject in need of such treatment an effective amount of GM-CSF.

Where the GM-CSF or G-CSF is administered systemically, for example intravenously or subcutaneously, it is contemplated that dose ranges comparable to those known for use to stimulate granulopoiesis in patients undergoing cancer chemotherapy are suitable. Where GM-CSF or G-CSF is to be applied regionally to the lung, it is contemplated that the dose range will be from 0.1 μg/kg body weight to 20 μg/kg body weight. The person skilled in the art will readily be able to determine suitable dose ranges by normal trial and error experimentation. In particular, the acceptable degree of toxicity at high doses will depend on the condition to be treated. Compositions for administration of GM-CSF or of G-CSF to the lung are also within the scope of the invention.

As will be discussed in detail below, we have surprisingly found that mice in which GM-CSF expression is disrupted are haematologically essentially normal, indicating that GM-CSF is not by itself required for development and maturation of granulocytes and monocytes/macrophages, at least in a steady-state situation. However, the increased susceptibility of the GM-CSF deficient mice to infection indicates that GM-CSF is required for "emergency" granulocyte and macrophage development. Similarly, mice in which G-CSF expression is disrupted are neutropaenic, but have essentially normal levels of monocytes/macrophages. Thus at least one other factor must be involved in steady state haemopoiesis, and the novel animals of the invention can be used to identify and isolate such factors.

Thus in a further aspect the invention provides a factor which is involved in regulation of steady-state haematopoiesis, and which is present in animals in which expression of GM-CSF or G-CSF is disrupted. Preferably the factor is also present in animals in which expression of both GM-CSF and G-CSF is disrupted, or in which expression of both GM-CSF and CSF-1 is disrupted.

As is well known in the art, such haematopoietic growth factors in mice have a high degree of homology with the corresponding factors in humans, and this homology is sufficient to enable a gene encoding a murine factor to be used as a probe for the isolation of the corresponding human factor. Even if the degree of homology is relatively low, iterative screening at low stringency can be used. Therefore this aspect of the invention also provides a gene encoding a factor involved in regulation of steady-state haematopoiesis, and which is present in animals in which expression of GM-CSF or G-CSF is disrupted, which can be used for isolation of the corresponding gene. Preferably the gene from the animal has at least 30% homology to the human gene, more preferably at least 50% homology, and even more preferably at least 90% homology.

For treatment of individuals with alveolar proteinosis, including congenital alveolar proteinosis, gene therapy may be the most appropriate course. Methods for such gene therapy are known in the art, given that the identity of the defective gene is known and that the appropriate DNA has been isolated. In a particularly preferred form, it is contemplated that intravenous administration of liposomal formulations of cDNA encoding GM-CSF will be used, as described for example by N. Zhu, D. Liggitt and R. Debs et al, Science, 1993 261 209: "Systemic Gene Expression After Intravenous DNA Delivery Into Adult Mice", the contents of which are herein incorporated by reference.

Since it is evident from our results that genetically-determined deficiency of a colony-stimulating factor leads to increased susceptibility to infections, especially Gram-negative pneumonias, the invention also provides a method of diagnosis of a colony-stimulating factor deficiency, comprising the step of testing a tissue or cell sample from a subject suspected of suffering from such a deficiency for the absence of the gene encoding said factor. Preferably the colony-stimulating factor is GM-CSF, but G-CSF and M-CSF are also included within the scope of the invention. The test may suitably be carried out using peripheral blood lymphocytes, but may also use tissue obtained by biopsy, for example from lung. A test may be carried out using methods which are known per se, such an polymerase chain reaction, or reaction with a probe labelled with a detectable marker, for example using in situ hybridisation.

In a sixth aspect, the invention provides targeting constructs for disruption of the genes encoding GM-CSF and G-CSF respectively, as described herein.

Figure 1:
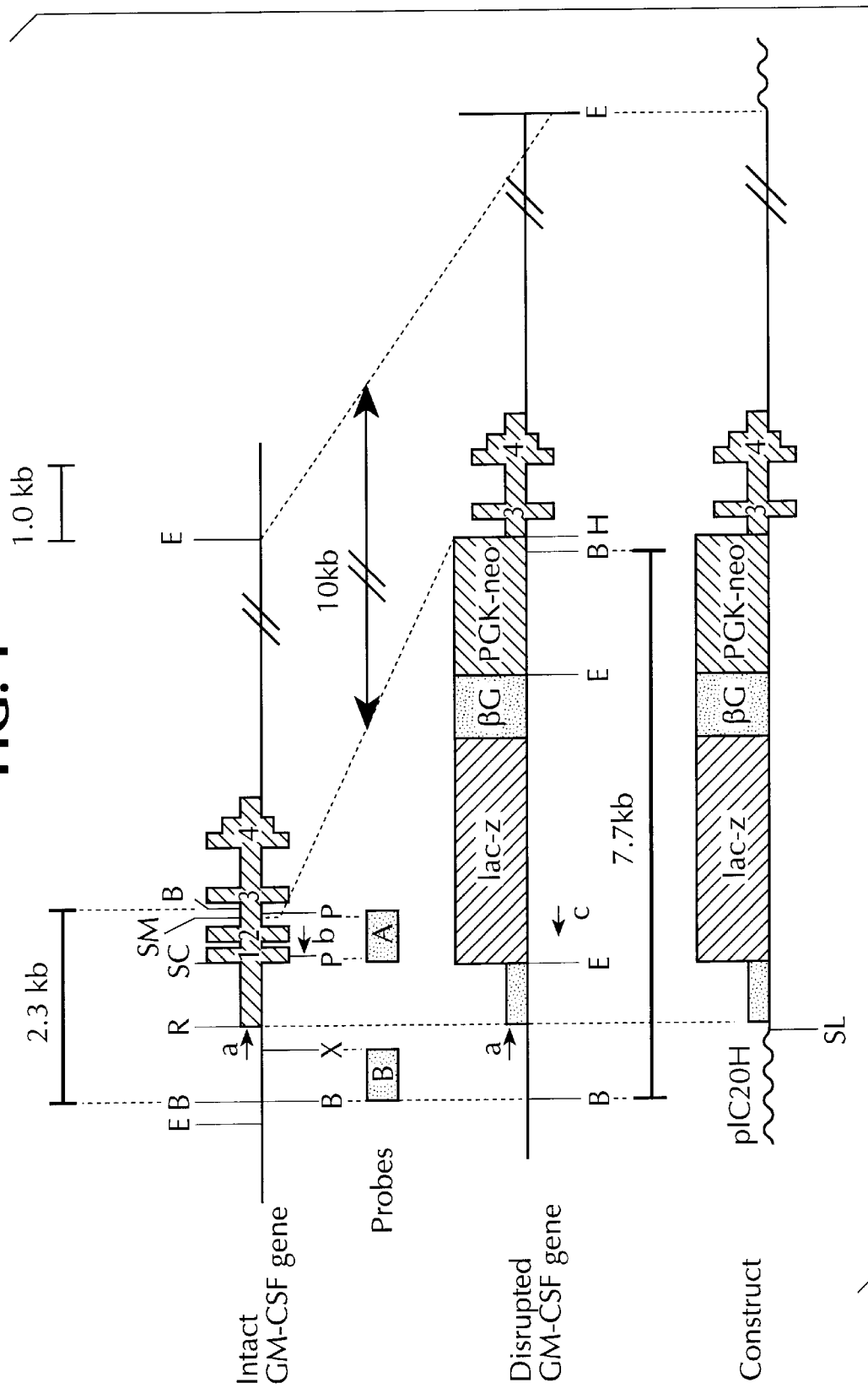
FIG. 1 shows the scheme used for generation of GM-CSF deficient mice, and the strategy for disruption of GM-CSF gene, showing the intact GM-CSF gene with 4 exons (1,2, 3&4), location of restriction enzyme sites (E=EcoRI, B=BglII, SC=ScaI, SM=SmaI, X=XmnI, P=PstI, H=HindIII, SL=SalI), probe A (external to construct, diagnostic for targeted disruption) and probe B (corresponding to deleted sequences) and sites of PCR primer hybridisation (a=Ed120, b=Ed121, c=NEB#1224, see text). In the disrupted allele, exons 1 and 2 and intron 1 are deleted, replaced by the E. coli 1ac-z gene, human β-globin 3' untranslated and polyA addition sequences (βG) and PGK-neo (see text).

A. Normal C57Bl/6 lung, central region (13 week, H&E X40)

B&C. GM−/− lung with moderate (B) and extensive (C) lymphoid hyperplasia around central and peripheral vessels (11 week, H&E X40)

D. Detail of alveoli in GM−/− lung with large foamy macrophages, neutrophils and eosinophilic alveolar debris (7 week, H&E X400)

E–H. Immunoperoxidase staining of perivascular mononuclear cells in GM−/− mouse lung (16 week, X200) with primary antibodies [specificity]: E, PBS [negative control]; F, RA3–6B2 [B220]; G, GK1.5 [CD4]; H, 53.6–7 [CD8] (same nodule in each panel)

I–K. Focus of infection with fungal element in GM−/− lung (16 week, X400): I, positive control for Grocott stain; J, 5–10 μm Grocott-positive fungal particles; K, PAS-positive fungal particles in same location of contiguous section L–N. Bacterial infections in GM−/− lungs: L, Gram stain control with Gram-positive and Gram-negative bacilli; M, Gram-positive coccobacilli in pneumonic consolidated area (7 week, X400); N, purulent acute *Pasteurella pneumotropica* lobar pneumonia in mouse dying at 4 weeks of age (H&E, X400)

O–Q. Features of 24 week GM−/− lung: granular refractile PAS-positive homogenous eosinophilc material in contiguous alveoli (O, H&B X400; P, PAS X400); Q, emphysematous area (arrowed) with persistent peri-bronchovascular lymphoid hyperplasia.

Figure 3:
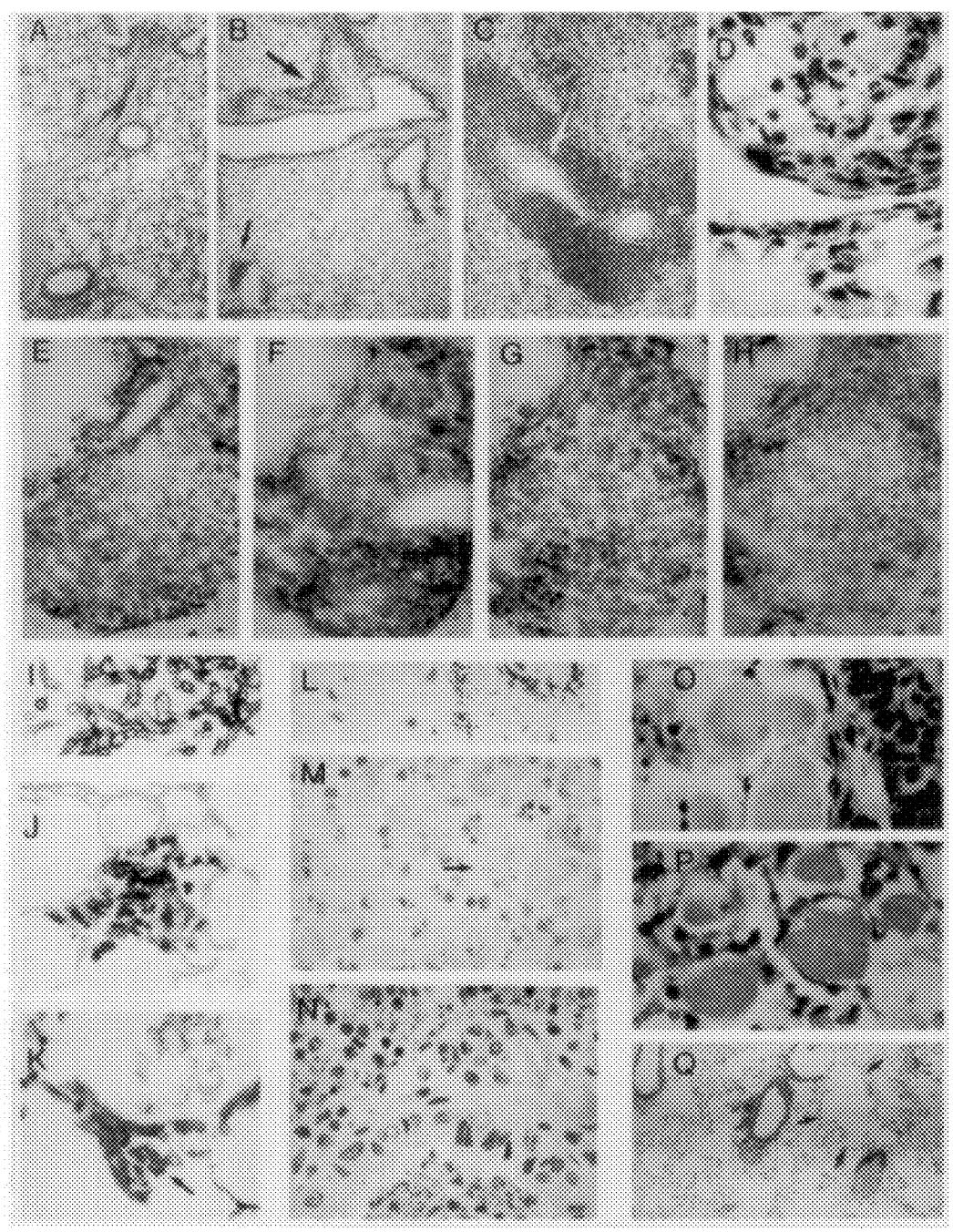
FIG. 3 shows typical appearances of lung histopathology in GM-CSF deficient mice.
Figure 4:
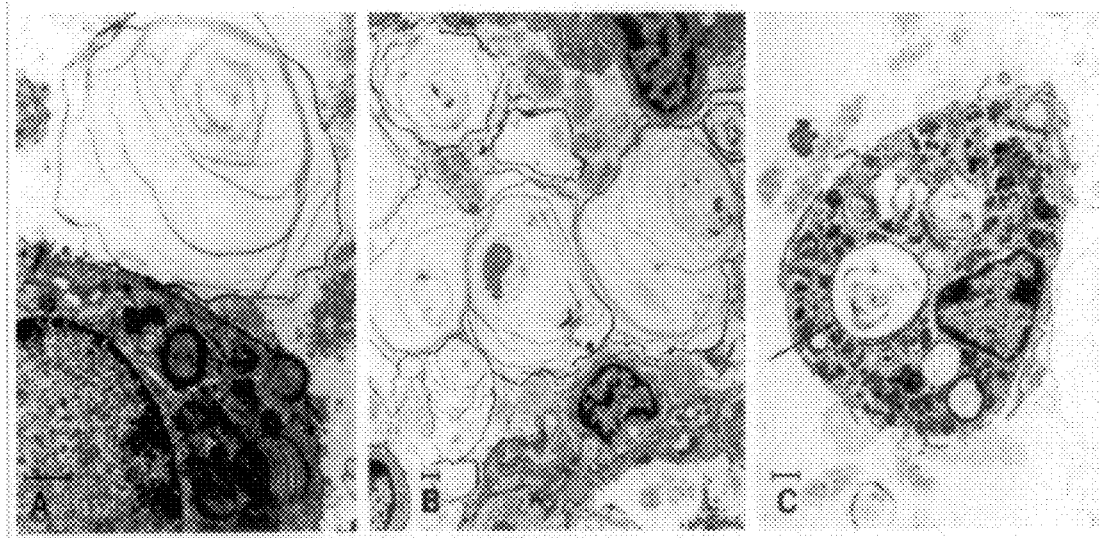

FIG. 4 shows the ultrastructural appearance of lungs from GM-CSF deficient mice. Electron microscopic sections of 24 week old GM−/− lung (same mouse as FIGS. 3O–Q). Solid bars indicate 1μm.

A. Type II surfactant-producing alveolar cell with characteristic intracytoplasmic lamellar bodies. The adjacent alveolus contains Type-C lamellar body.

B. Numerous intra-alveolar Type-C lamellar bodies with characteristic "onion" appearance.

C. Intra-alveolar macrophage with phagosomes containing "onion" structures resembling Type-C lamellar bodies.

Figure 5A:
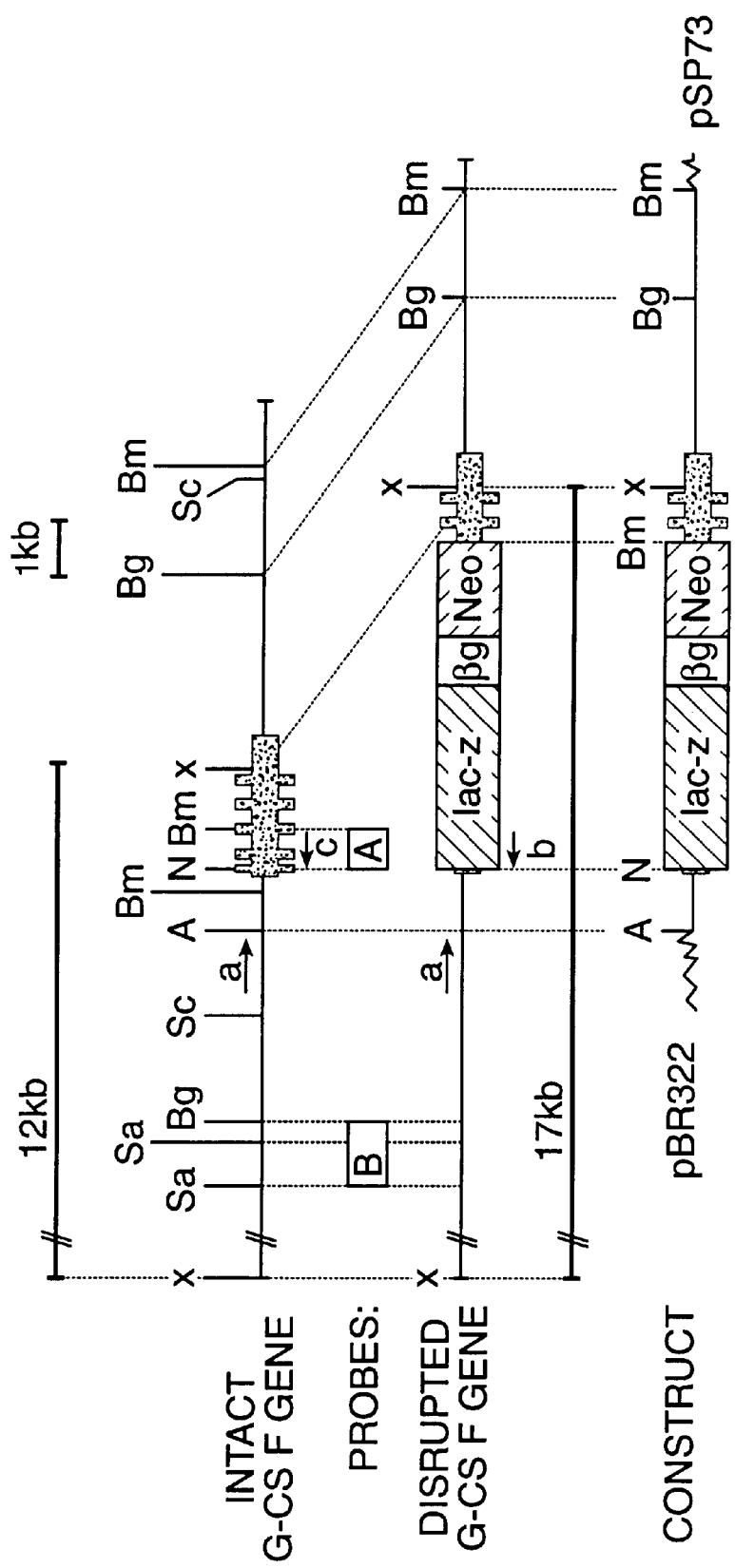

FIG. 5A shows the screening strategy used to distinguish between wild-type and disrupted G-CSF alleles by genomic Southern analysis of XbaI digests of DNA. Hatched regions represent genomic sequences flanking the G-CSF gene. Black regions represent the exons of the G-CSF gene, and βb represents 3' untranslated sequences and polyA addition motif from the human β-globin gene.

Figure 5B:
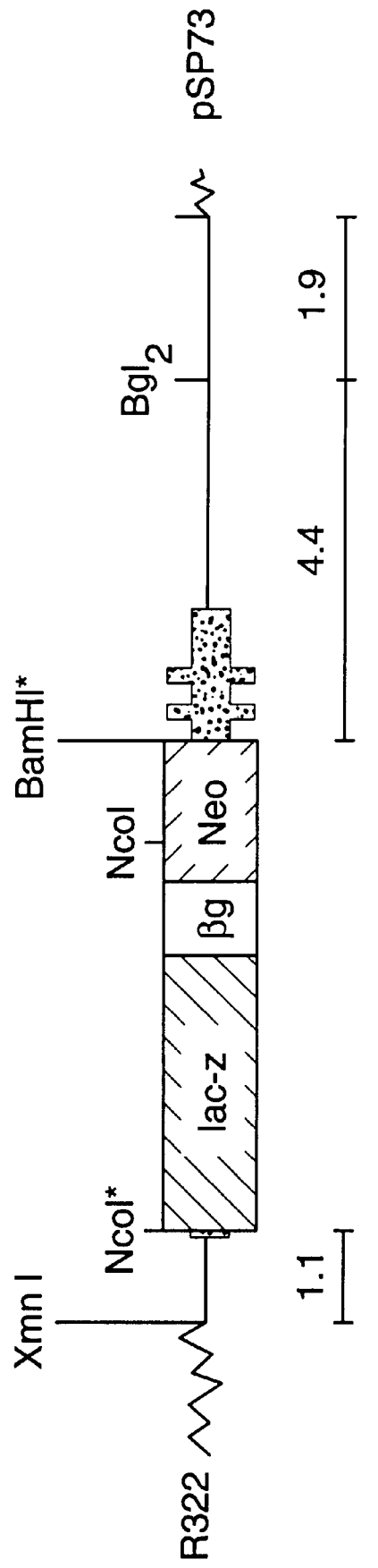

FIG. 5B illustrates the targeting construct, designated pKOGCSF3b, used to generate the ES cell line 5.4 from which the G-CSF deficient animals were derived.

Figure 6:
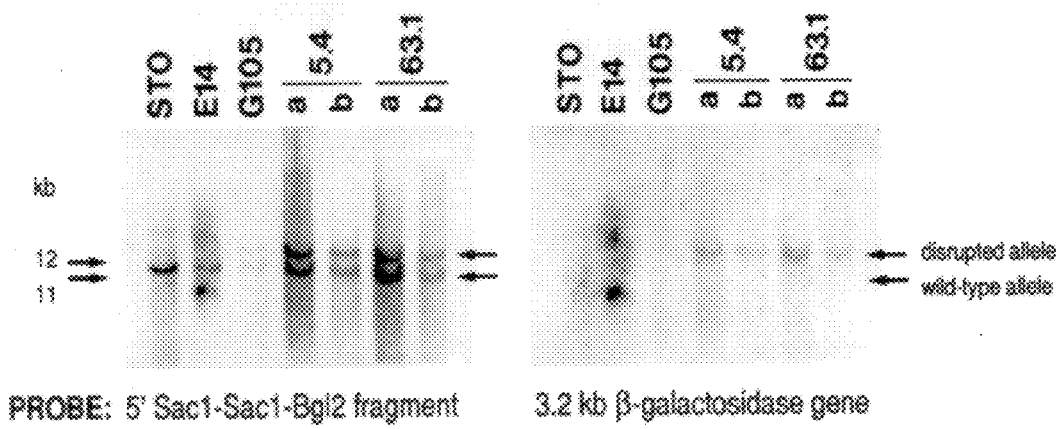

FIG. 6 shows Southern blot analysis of the ES cell line 5.4, from which founding G-CSF+/− chimeras were generated. The probe used in the left hand panel hybridizes with a region outside the targeting vector, and is diagnostic for homologous integration of the targeting vector at one G-CSF allele. The probe for β-galactosidase, used in the right-hand panel, hybridses exclusively with a region within the disrupted allele.

Figure 7B:
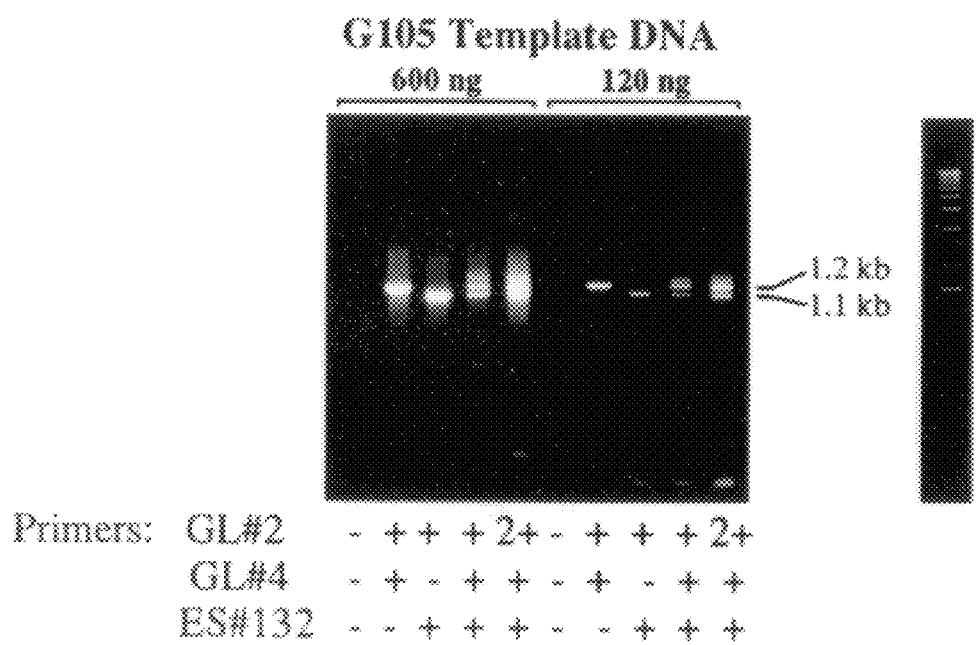

FIG. 7 shows the PCR-based screening strategy for the disrupted G-CSF allele. The primers are described in the text.

Figure 8:
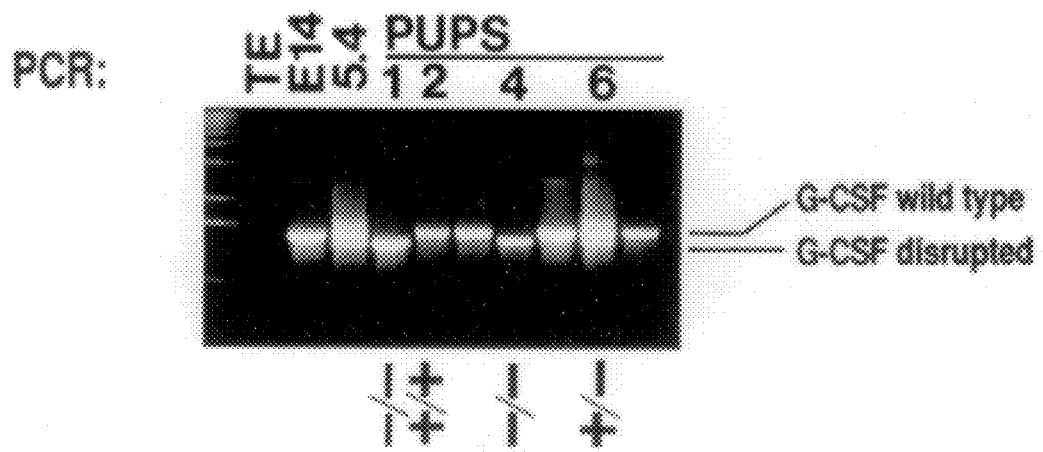

FIG. 8 shows PCR analysis of DNA from tail tissue of G-CSF +/− chimeras and their progeny.

Figure 9:
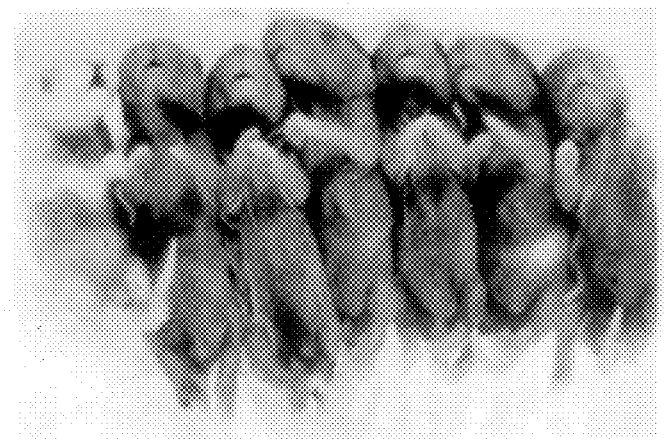

FIG. 9 shows pups born from matings of heterozygous G-CSF+/− parents.

Figure 10:
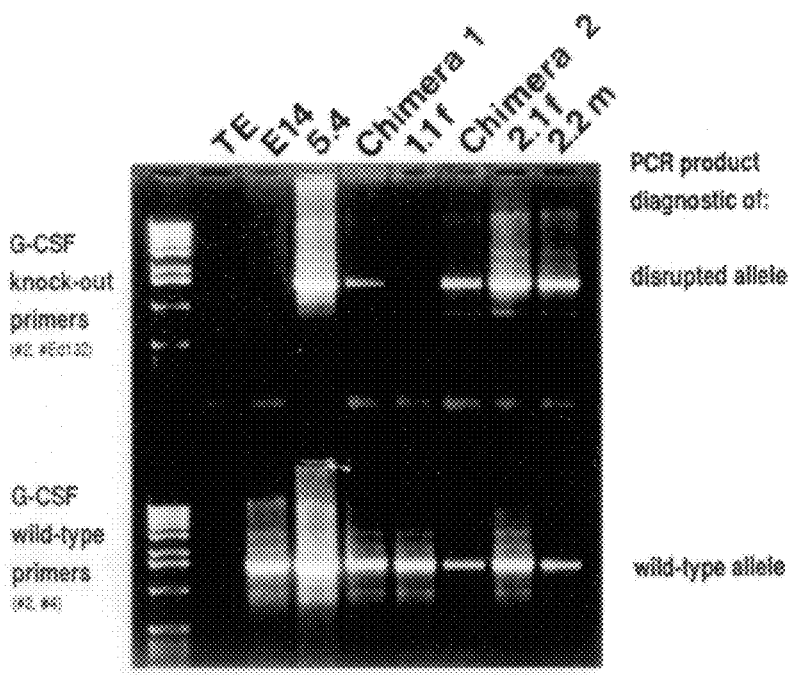

FIG. 10 shows PCR analysis of tail tisuse DNA from G-CSF −/+ chimeras and their progeny, demonstrating germline transmission.

Figure 11:
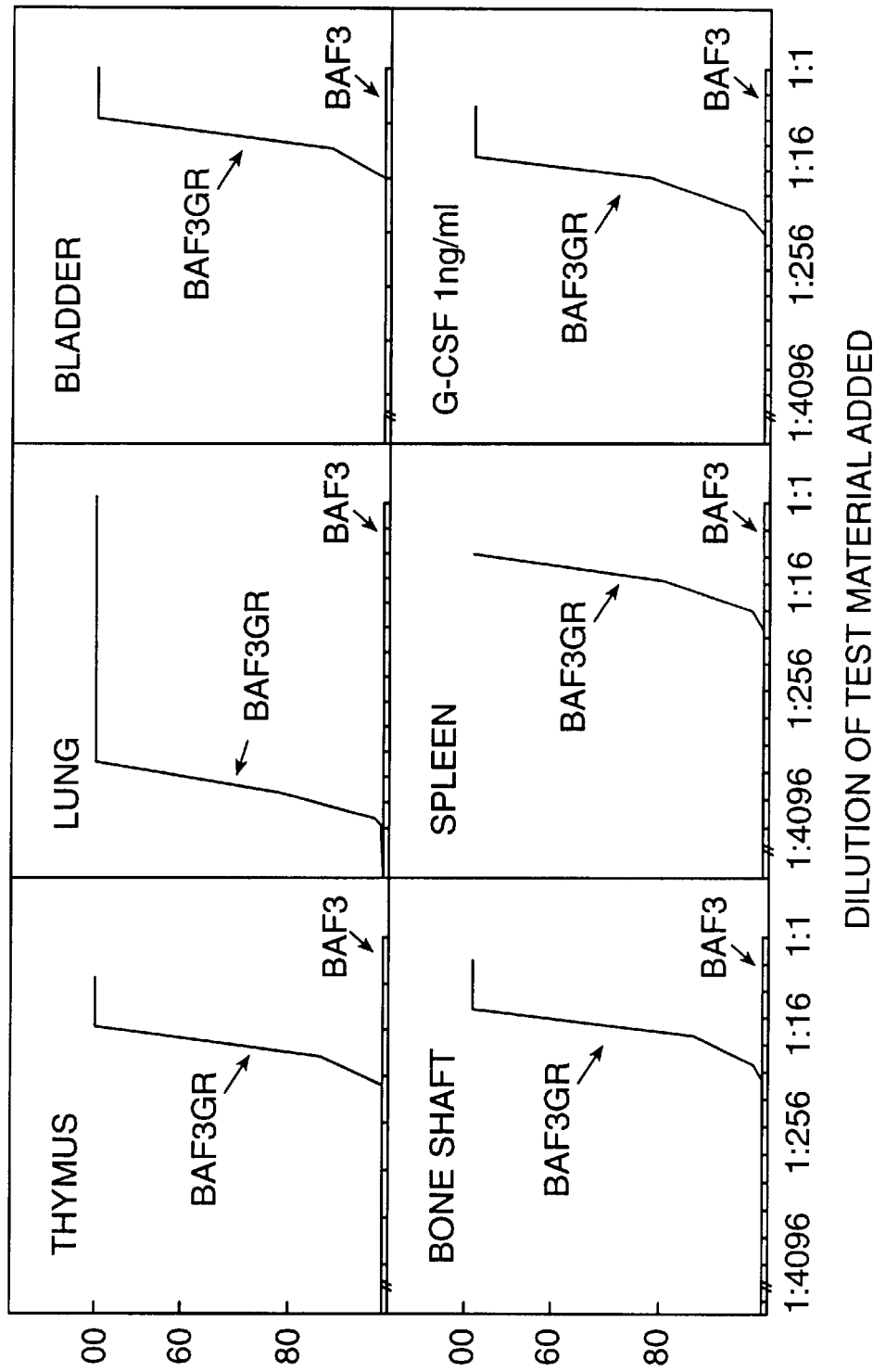

FIG. 11 shows results of assays on conditioned media from organs of G−/−, GM−/− and wild-type mice.

Figure 12:
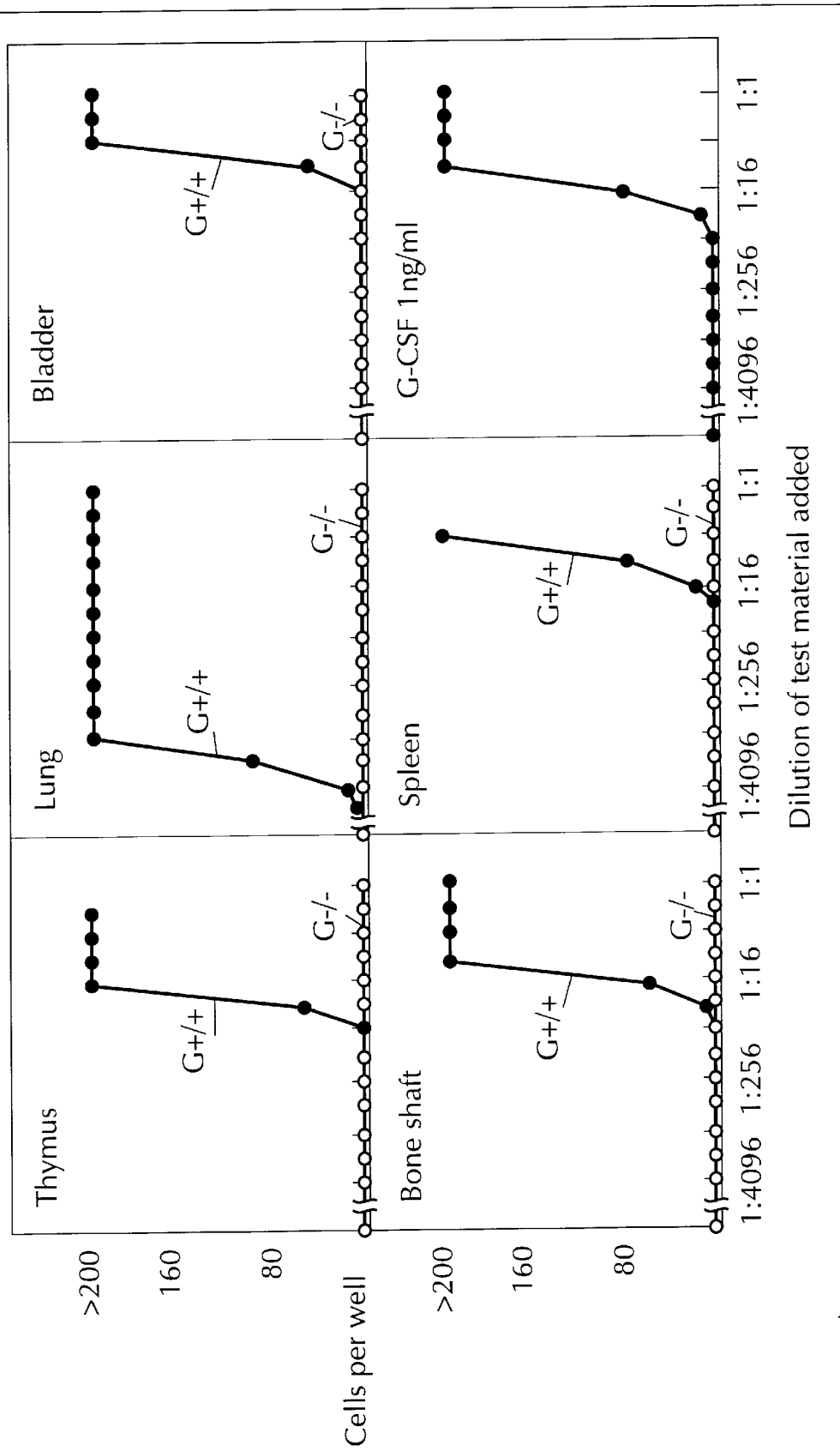

FIG. 12 shows that G−/− mice are unable to produce G-CSF. Results of conditioned media from organs of G+/+ (wild-type) mice are compared with those of G−/− and GM−/− mice.

DETAILED DESCRIPTION OF THE INVENTION

The invention will now be described by way of reference only to the following non-limiting examples, and to the figures.

Abbreviations

The abbreviations used herein are as follows:

| | |
|---|---|
| CSF | colony-stimulating factor |
| G-CSF | granulocyte colony-stimulating factor |
| GM-CSF | granulocyte-macrophage colony-stimulating factor |
| M-CSF | macrophage colony-stimulating factor |
| ES cells | embryonic stem cells |
| ZL | interleukin |
| PCR | polymerase chain reaction |
| Taq polymerase | *Thermuus aquaticus* DNA polymerase |
| ELISA | enzyme-linked immunoadsorbent assay |
| H&E | haematoxylin and eosin stain |
| PAS | Periodic acid-Schiff stain |
| SCM | spleen-cell conditioned medium/media |
| SCF | stem cell factor |
| G418 | neomycin |
| bp | base pairs |

Cell lines, vectors and antibodies
Cell lines used herein are as follows:

| | |
|---|---|
| COS cells | cell line of monkey origin able to support replication of vectors comprising the SV40 origin of replication. |
| E14 | ES cells derived from mice of strain 129/OLA (see Reference 17) |
| FDC-P1 | cell line which responds to GM-CSF and IL-3 |
| 32-D | cell line which responds specificaly to IL-3 |

All these lines are well known in the art.

Vectors used herin are as follows: pIC20H
Antibodies used herein are as follows:

MATERIALS AND METHODS

| | |
|---|---|
| MP1-22E9 | specific for GM-CSF |
| MP1-31G6 | second antibody used in ELISA |
| RA3-6B2 | specific for B cells |
| 187.1 | specific for B cells |
| GK1.5 | specific for T helper cells |
| 59.6-7 | specific for T suppressor cells |
| 53-7.8 | specific for pan T cell marker |

Statistics

Data are given as mean ± standard deviations. To test for statistically significant differences, the unpaired Student's t-test and Chi-squared test were used.

Generation of targeted ES cell colonies and chimeric mice

In their general aspects, the methods employed are known per se. Methods for isolation and injection of mouse blastocysts, and implantation into host females for generation of transgenic mice, are extensively reviewed in the volume "Manipulating the Mouse Embryo—A Laboratory Manual" by B. Hogan, F. Costantini and E. Lacy (Cold Spring Harbor Laboratory, 1986).

EXAMPLE 1

GM-CSF targeting vector and isolation of targeted ES cell clones

The GM-CSF targeting vector, illustrated in FIG. 1 contained from 51' to 3' in plasmid pIC20H, approximately 900 bp of the GM-CSF promoter (RsaI-ScaI) (13,14), the *E. coli* lac-z gene modified at the 5' end, an approximately 700 bp fragment of the 3' untranslated region and polyA addition motif from the human β-globin gene (EcoRI-AccI), the PGK-neo selectable marker (15), and approximately 10 kb of GM-CSF genomic sequence from a previously isolated lambda clone (14). The targeting vector was constructed to delete GM-CSF exons 1 and 2 and intron 1 between ScaI and SmaI sites because in previous studies, cDNAs with this region deleted produced no GM-CSF activity when over expressed in COS cells (16). The vector was linearized at a SalI site in the pIC20H polylinker prior to electroporation into E14 embryonal stem (ES) cells derived from mice of the strain 129/OLA (17), which were maintained and subsequently selected in medium containing the antibiotic G418, as previously described (18). After 8 days of G418 (Geneticin; Gibco) selection, individual G418-resistant colonies were cloned and replated.

The polymerase chain reaction (PCR) was used to screen DNA from each ES cell colony for integration of a targeting vector by homologous recombination. The PCR primers were:

| | |
|---|---|
| "a" | SEQ ID NO:1<br>5'-CCAGCCTCAGAGACCCAGGTATCC-3', corresponding to sequence 5' of the RsaI site in the GM-CSF promoter; |
| "b" | SEQ ID NO:2<br>5'-GTTAGAGACGACTTCTACCTCTTC-3', corresponding to sequence in exon 2 of the GM-CSF gene in the region deleted by targeted construct integration; and |
| "c" | a M13 (-47) 24 mer sequencing primer (New England Biolabs, Beverly, MA, #1224), corresponding to the 5' region of the E. coli lac-z gene. |

These are illustrated in FIG. 1. In PCR reaction mixtures, primers "a" and "b" generate a 1.2 kb product from wild-type DNA, and "a" and "c" a 1.0 kb product from DNA containing a correctly integrated targeted construct. PCR reaction mixtures (20µl) contained approximately 250 ng DNA, 67 mM Tris-HCl (pH 8.8), 16.6 mM $(NH_4)_2SO_4$, 0.45% Triton X-100, 200µg/ml gelatin, 1.5 MM $MgCl_2$, 250 µM of each deoxynucleoside triphosphate, 12.5 ng of each primer and 1.5 U of Tag polymerase.

Following initial denaturation (95° C. [150s]), 40 amplification cycles were performed (95° C. [50s], 60° C. [50s], 72° C. [60s]). The structure of targeted alleles identified by PCR was confirmed by Southern blot analysis of DNA from tail tissue of mice homozygous for the disrupted GM-CSF allele, which were generated as described in Example 9 below. BglII-digested DNA was probed with a radiolabelled DNA fragment corresponding to GM-CSF genomic sequences which were deleted from the targeting construct (probe A, FIG. 1, PstI-PstI fragment) to verify that these sequences were absent from the presumptive GM-CSF homozygous null mice, and reprobed with a probe B (FIG. 1) corresponding to sequences lying outside the targeting construct (the BglII-XmnI genomic fragment 5' of the RsaI site in the GM-CSF promoter).

EXAMPLE 2

Generation of Chimeric mice

Two clonally independent ES cell lines (designated GM4 and GM6) with a targeted GM-CSF gene disruption were selected for injection into C57BL/6 mouse blastocysts. The resulting male chimeras from both cell lines transmitted the disruptive mutation through the germline in matings with females from a C57BL/6 background, to generate heterozygous male and female progeny. These heterozygous progeny were interbred to generate mice homozygous for the disruptive mutation. GM-CSF genotypes of mice have been designated as follows:

wild-type, GM+/+;
heterozygous GM+/−;
homozygous GM−/−.

The GM-CSF status of mice was routinely assessed by PCR analysis of DNA from tail tissue of the mice. GM−/− mice were subsequently bred from GM−/−×GM−/− matings, and to generate similarly outbred 129/OLA×C57BL/6 GM+/+ control mice, GM+/+ mice were bred from first- and second-generation GM+/+ littermates. Mice were kept in a conventional animal house. Except where stated, observations come from the GM4 lineage.

EXAMPLE 3

Verification of GM-CSF gene disruption

Figure 2A:
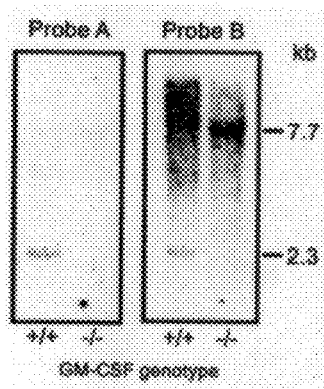
FIG. 2 illustrates how deletion of GM-CSF exons 1–2 results in lack of GM-CSF immunoreactivity and bioactivity in spleen conditioned media. Southern blot of BglII digested tail DNA from PCR-genotyped GM+/+ and −/− mice probed first with probe A (see FIG. 1A), confirming that deleted exons are present only in wild-type mouse, then reprobed without washing with probe B, confirming that the −/− mouse is homozygous for the disrupted GM-CSF allele and lacks the deleted sequences. Levels of immunoreactive (panel B) and bioactive (panel C) GM-CSF (solid columns) and bioactive IL-3 (open columns) in media conditioned by concanavalin-A and IL-2 stimulated splenocytes are shown for individual GM+/+ and GM−/− mice. In panel C, shaded column shows GM-CSF bioactivity after neutralisation with an anti-Gm-CsF antibody.

To confirm the structure of the targeted allele in GM−/− mice, Southern blotting analysis was performed on BglII-digested tail DNA from randomly-selected GM+/+ and GM−/− mice which had been genotyped by PCR, using a probe corresponding to the exon 1 and 2 sequences deleted in the targeted GM-CSF gene. As expected, GM+/+ but not GM−/− tail DNA contained a 2.3 kb species hybridizing with the exon 1–2 probe. GM−/− DNA contained the predicted 7.7 kb species when hybridized with a probe corresponding to sequences lying outside the targeting vector, as shown in FIG. 2A.

EXAMPLE 4

Spleen cell-conditioned media and GM-CSF assays

Spleen cell-conditioned media were prepared as previously described (19), except that the splenocytes were stimulated with concanavalin-A (5µg/ml, Boehringer-Mannheim, Germany) and interleukin-2 (100U/ml, Amgen, Thousand Oaks, CA). To assay immmnoreactive GM-CSF, an ELISA was used with the antibodies MP1-22E9 and biotinylated MP1-31G6 (Pharmingen, San Diego, Calif.) with an avidin-biotinylated horseradish peroxidase (Dako, Copenhagen, Denmark) detection system with a sensitivity of 50 pg/ml. To assay bioactive GM-CSF, the proliferative response of FDC-P1 cells, measured by $^3$H-thymidine incorporation, was used, adjusting for interleukin-3 (IL-3) bioactivity on 32-D cells, using methods previously described (20). The MP1-22E9 neutralising antibody was used to confirm the specificity of the putative GM-CSF bioactivity. Standards used were recombinant murine GM-CSF (Schering-Plough, Kenilworth, N.J.) and IL-3 ($10^7$ U/mg, Boehringer- Mannheim, Germany).

Figure 2B:
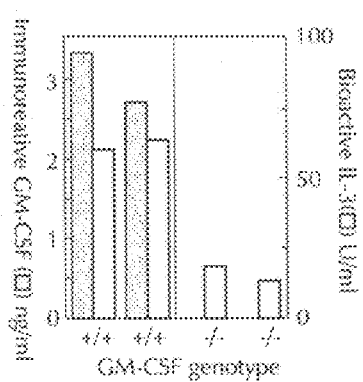

To confirm that tissues from GM−/− mice lacked GM-CSF, spleen cell-conditioned media (SCM) made from GM+/+ and GM−/− splenocytes were assayed for immunoreactive and bioactive GM-CSF. Using a GM-CSF ELISA, no immunoreactive GM-CSF was detected in SCM from GM−/− splenocytes while SCM from by GM+/+ splenocytes contained more than 2700 pg/ml of GM-CSF. These results are summarized in FIG. 2B. To assay for bioactive GM-CSF, the proliferative response of FDC-P1 cells, which respond to GM-CSF and IL-3, was assayed in parallel to that of 32-D cells, which respond only to IL-3.

There was no detectable bioactive GM-CSF in SCM from GM−/− splenocytes, whereas GM+/+ SCM contained more than 100 pg/ml bioactive GM-CSF which was at least 95% neutralised by an anti-GM-CSF antibody. To confirm the potency of these SCM, all were shown to contain bioactive IL-3, although SCM from GM−/− mice contained less IL-3 than did SCM from control mice (GM−/−, 16±2 U/ml, n=4; GM+/+, 49±20 U/ml, n=4; p<0.01). The inability of GM−/− tissues to produce GM-CSF in vitro was confirmed by studies on muscle and kidney conditioned media, using microwell assays of FDC-P1 cells (3).

EXAMPLE 5

Viability and fertility

From initial matings of GM+/− mice, litters of 10±3 pups (n=8, GM6) resulted, with the genotypes GM+/+, +/− and −/− represented in approximately Mendelian ratios amongst live births surviving to weaning, indicating that there was no selective fetal or neonatal loss of GM−/− pups. Survival of mice from initial litters was normal amongst GM−/− pups (>91%, n=35) compared to their GM+/+ littermates (>88%, n=17), with a median follow-up for GM−/− mice of 220 days [range 0–3343] days and for GM+/+ mice of 209 days [range 0–3133] days; median survival has not been attained. Past-mortem examination of the two dead GM−/− adults in this cohort indicated that one, which died at 153 days, had lymphoid leukaemia and the other, which died at 167 days, had hepatitis; both displayed the characteristic GM-CSF deficiency lung disease which is described in detail below. From initial matings of male and female GM−/− mice, litters of 9±1 pups (n=5) resulted, indicating that GM-CSF deficiency did not grossly impair fertility or fecundity.

EXAMPLE 6

Haematological analysis of GM-CSF deficient mice

Haemoglobin, total leukocyte and platelet estimates were performed on 1:4 dilutions of eye-bleed samples on a Sysmex-K1000 automated counter, and manual 100-cell leukocyte differential counts were performed on May-Grunwald/Giemsa stained smears.

Progenitor cells were assayed in semisolid agar cultures of bone marrow, spleen or peritoneal cells by a standard method, as previously described (19,21). Colony formation was stimulated by purified recombinant bacterially-synthesized growth factors at the following final concentrations: human G-CSF [10 ng/ml], murine GM-CSF [10 ng/ml], murine IL-3 [10 ng/ml], murine M-CSF (CSF-1) [10 ng/ml] rat stem cell factor [100 ng/ml], murine IL-6 [500 ng/ml], and spleen cell-conditioned medium (10%). Colonies were typed on stained whole-plate preparations as previously described (21).

The haematological parameters of peripheral blood of 6–7 weeks GM−/− mice showed no significant difference from those of blood of GM+/+ littermates, as illustrated in Tale 1.

TABLE 1

Haematological Analysis of GM-CSF - deficient mice

|  | GM+/+ | GM−/− |
|---|---|---|
| Haemoglobin (g/l) | 162 ± 7 | 163 ± 5 |
| total leukocytes (×10$^9$ cells/l) | 5.9 ± 1.0 | 7.4 ± 2.4 |
| neutrophils (×10$^9$ cells/l) | 1.1 ± 0.3 | 1.2 ± 0.6 |
| lymphocytes (×10$^9$ cells/l) | 4.7 ± 1.1 | 6.0 ± 2.0 |
| monocytes (×10$^9$ cells/l) | 0.12 ± 0.10 | 0.13 ± 0.13 |
| eosinophils (×10$^9$ cells/l) | 0.09 ± 0.06 | 0.13 ± 0.13 |
| platelets (×10$^9$ cells/l) | 838 ± 105 | 822 ± 109 |

10 mice in each group were tested
Results are expressed as mean ± S.D.

GM−/− mice tended to have greater variation in their granulocyte levels, as illustrated by the granulocyte levels of 5–7 week mice: GM−/−1.7±1.5×10$^9$/l [n=33, range 0.2–6.6]; GM+/+1.3±0.7×10$^9$/l [n=15, range 0.29–3.1], with 24% of GM−/− mice having neutrophils greater than 2×10$^9$/l compared to 15% of GM+/+. Spleens of GM−/− mice showed increased variability in mass (e.g. spleen mass of 6 weeks mice, n=6/group: GM+/+106±9 [range 94–120] mg; GM−/−, 114±42 [range 64–191] mg).

Haematopoiesis was evaluated in five pairs of 6–8 week GM+/+ and −/− mice. Femoral cellularity was equivalent (GM+/+34.0±5.3×10$^6$, GM−/−27.4±7.0×10$^6$ cells/femur, n=3) and the myeloid:erythroid ratios were equivalent (20±2 and 17±6% erythroid cells respectively). The results of analysis of marrow progenitor cells responsive to various stimuli, summarized in Table 2, revealed no major difference in total progenitor cell frequency, and colony subtyping indicated no differences in frequencies of granulocyte, granulocyte-macrophage, macrophage, eosinophil, megakaryocyte, erythroid and blast marrow progenitor cells. To assess the role of GM-CSF in the phenomenon of "spontaneous" in vitro colony formation, crowded unstimulated cultures of up to 2×10$^5$ GM−/− marrow cells/ml were established; colony formation was somewhat reduced, indicating that "spontaneous" colony formation is not solely dependent on in vitro GM-CSF production.

TABLE 2

Haematopoietic progenitor cells in GM-CSF deficient mice

| Cells cultured (n) | Stimulus | Total colonies (mean ± S.D. | |
|---|---|---|---|
|  |  | GM+/+ | GM−/− |
| 25,000 bone marrow (5) | GM-CSF | 59 ± 12 | 51 ± 19 |
|  | G-CSF | 19 ± 3 | 15 ± 7 |
|  | M-CSF | 64 ± 16 | 59 ± 25 |
|  | IL-3 | 68 ± 12 | 68 ± 19 |
|  | SCF | 29 ± 3 | 22 ± 13 |
|  | IL-6 | 18 ± 8 | 18 ± 10 |
|  | SCF + GM-CSF | 66 ± 12 | 63 ± 26 |
| 200,000 bone marrow (5) | Saline | 79 ± 62 | 39 ± 44 |
| 100,000 spleen (3) | GM-CSF | 3 ± 4 | 8 ± 2 |
|  | SCF | 0 | 4 ± 2* |
|  | SCF + GM-CSF | 3 ± 1 | 20 ± 2* |
|  | SCM | 4 ± 3 | 18 ± 2* |

(n) indicates the number of individual mice studied
*indicates p < 0.001.

Cultures were stimulated by: granulocyte-macrophage-CSF (GM-CSF), granulocyte-CSF (G-CSF), CSF-I (H-CSF), interleukin-3 (IL-3), stem cell factor (SCF), interleukin-6 (IL-6), spleen cell-conditioned medium (SCM), or a combination of these.

Genotype is indicated as wild-type (GM+/+) or GM-CSF deficient (GM−/−).

The spleen masses for these groups of mice were: GM+/+, 64±8 mg; GM−/−, 114±22 mg (p<0.001).

Analysis of splenic haematopoiesis showed a 3 to 6 fold increase in frequency of progenitor cells in GM−/− mice, and as the GM−/− spleens were significantly larger, this represented an absolute increase in number of splenic progenitor cells (Table 2). Peritoneal washings recovered 6.0±1.4×10$^6$ and 5.1±1.4×10$^6$ cells from GM+/+ and GM−/− mice respectively; these washings comprised 65% macrophage in GM+/+ and 63% macrophages in GM−/− mice.

EXAMPLE 7

Histological examination of GM-CSF deficient mice and characterisation of pulmonary disease Formalin-fixed paraffin-embedded sections of mouse organs were stained using standard techniques with haematoxylin and eosin (H&E), and selected sections were stained with the Grocott methenamine silver and periodic-acid-Schiff (PAS) stains, and Ziehl-Neelson and Wade-Fite acid fast stains. Immunoperoxidase staining of lung tissue was performed using a standard method (22) on 4 μm frozen sections, with the following antibodies: RA3-6B2 [specific for B220] (23), 187.1 [specific for κ light chain] (24), GK1.5 [specific for CD4] (25), 53.6–7 [specific for CD8] (26), and 53–7.8 [specific for CD5] (Pharmingen, San Diego, Calif.). For electron microscopy, random strips of fresh lung tissue were immersion-fixed in 2.5% glutaraldehyde in 1% sodium cacodylate buffer (pH 7.4), postfixed in 2% aqueous osmium tetroxide, and embedded in Araldite-Epon resin using standard techniques. Thin sections were stained with alkaline lead citrate and uranyl acetate, and viewed in a Jeol 1200EX electron microscope.

Histological sections from GM−/− mice aged 1 day to 24 weeks and age-matched GM+/+ controls of age were reviewed. No major differences between GM+/+ and GM−/− were evident in haematopoietic tissues; marrow cellularity was normal and some GM−/− spleens were enlarged with hyperplasia of both red and white pulp. Whilst at birth the lungs of GM−/− and GM+/+ animals were indistinguishable, within the first 3 weeks of post-natal development striking abnormalities were evident in the lungs of GM−/− mice. Individual lungs from GM−/− mice consistently showed focal aggregates of lymphoid cells in peribronchial and perivascular areas, but little infiltration of alveolar septa; typical results are shown in FIG. 3A–C. Immunoperoxidase staining of 12–16 week GM−/− lungs showed these cells to be predominantly B-lymphocytes on the basis of positive staining for B220 and κ-light chain. About 20% of lymphocytes were T-cells, predominantly of the CD4+type (FIG. 3E–H). The lymphoid foci were particularly marked around large hilar vessels, occasionally assuming a follicular organization, but the cells exhibited little mitotic activity. The foci characteristically extended peripherally around small bronchioles and arterioles.

Focal consolidation was prevalent, and consisted of an intensely eosinophilic alveolar exudate containing numerous mature and fragmented neutrophils and macrophages (e.g FIG. 3D,M,N). Associated bronchioles contained purulent exudate. In almost every GM−/− mouse of up to 6 weeks of age, acute inflammatory areas were found in the distal tips of the pulmonary lobes. Lobar consolidation was frequently observed (FIG. 3M&N). In lungs of older mice (6–12 weeks), the lymphoid hyperplasia predominated; alveoli contained large foamy macrophages and granular debris, and foci of acute inflammation, comprising aggregates of up to 50 neutrophils and mononuclear cells, were sometimes seen (FIG. 3D). Granular, eosinophilic, PAS-positive material within alveoli was present in all lungs examined (e.g. FIG. 3D&K), apparently accumulating and becoming confluent in some alveoli by as early as 3 weeks. This material was present until at least 6 months of age, and in some areas of 12–24 week GM−/− lungs contiguous alveoli containing this material resembled the appearances of alveolar proteinosis (FIG. 3O&P).

Ultrastructurally, surfactant-producing type-II alveolar cells were readily identified by their characteristic cytoplasmic lamellar bodies (FIG. 4A); the alveolar debris included numerous type-C lamellar bodies (FIG. 4B), and these onion-like bodies were seen within phagosomes of intraalveolar macrophages (FIG. 4C).

Peripherally, the alveolar spaces of lungs from older mice (24 weeks) lungs were large, suggesting an emphysematous process (FIG. 3Q). One 4 week-old GM−/− mouse died with florid lobar pneumonia (FIG. 3N) from which *Pasteurella pneumotropica* was isolated, corresponding to Gram-negative organisms evident in lung sections. A survey of GM−/− lungs with Grocott and PAS stains identified foci of 5–10 μm diameter fungal elements in 3/15 GM−/− lungs but 0/7 GM+/+ lungs (e.g. FIG. 3I–K). Surveys of sections with Gram stain identified large numbers of Gram-positive coccobacilli in one pneumonic area (FIG. 3L&M). No mycobacterial infections were evident with Ziehl-Neelson and Wade-Fite stains. One 6 week-old GM−/− mouse had developed a chronic pulmonary abscess with an organized wall lined by foamy macrophages and containing neutrophil-rich pus.

EXAMPLE 8

GM-CSF Deficient Mice Can Be Used to Test Host Response to Infection

Ten wild-type and ten GK-CSF deficient mice were challenged by intravenous injection with *Listeria monocytogenes*, at a dose of $5\times10^3$ colony, forming units per mouse. Haematological parameters and bacterial counts in the liver and spleen of mice sacrificed at day 1 and day 5 after infection are summarised in Table 3.

TABLE 3

Haematological Response to Listeria Infection

| Haematological Parameter | Before injection | | Day 1 | | Day 5 | |
|---|---|---|---|---|---|---|
| | GM+/+ (10) | GM−/− (10) | GM+/+ (10) | GM−/− (10) | GM+/+ (10) | GM−/− (10) |
| Haemoglobin g/L | 162 ± 7 | 163 ± 5 | 148 ± 9 | 152 ± 13 | 134 ± 6 | 127 ± 6 |
| Platelets × $10^9$/L | 838 ± 105 | 822 ± 109 | 750 ± 96 | 710 ± 99 | 776 ± 375 | 352 ± 340 |
| Total White Cells × $10^9$L | 5.9 ± 1.0 | 7.4 ± 2.4 | 10.9 ± 3.5 | 8.3 ± 2.0 | 11.8 ± 1.6 | 5.2 ± 2.2 |
| neutrophil | 1.1 ± 0.3 | 1.2 ± 0.6 | 4.6 ± 1.4 | 1.5 ± 0.9 | 3.4 ± 1.1 | 1.14 ± 0.55 |
| lymphocytes | 4.7 ± 1.1 | 6.0 ± 2.0 | 6.3 ± 2.3 | 6.0 ± 1.4 | 7.3 ± 0.9 | 3.5 ± 2.1 |
| monocytes | 0.12 ± 0.10 | 0.13 ± 0.13 | 0.18 ± 0.25 | 0.12 ± 0.13 | 1.11 ± 0.18 | 0.55 ± 0.25 |
| Eosinophils | 0.09 ± 0.06 | 0.13 ± 0.13 | 0.11 ± 0.13 | 0.12 ± 0.15 | 0.03 ± 0.06 | 0 |

TABLE 3-continued

| | | Listeria organism counts (log mean ± SD) | | | |
|---|---|---|---|---|---|
| | | (5) | (5) | (5) | (5) |
| Spleen | per organ | 5.00 ± 0.48 | 5.11 ± 0.35 | 2.65 ± 0.10 | 5.98 ± 1.44 |
| | per gm | 6.05 ± 0.45 | 6.11 ± 0.40 | 3.26 ± 0.18 | 6.76 ± 1.66 |
| Liver | per organ | 4.17 ± 0.51 | 5.02 ± 0.40 | 2.04 ± 0.41 | 6.15 ± 1.92 |
| | per gm | 4.24 ± 0.51 | 5.03 ± 0.46 | 1.96 ± 0.39 | 6.16 ± 2.00 |

Results for the haematological parameters are presented as mean±standard deviation, while those for organism counts are presented as log mean±standard deviation. The figures in brackets represent the number of mice in each group.

On Day 5, 2 GM−/− mice were dead, with organism counts of greater than $10^8$ per organ for spleen or liver. The surviving GM−/− animals had 5.66±0.95 organisms g/spleen and 4.81±1.07 organisms/liver, which was still much higher than the counts for GM+/+.

Haematologically, the GM−/− mice showed a perturbed response, with an impairment of neutrophil mobilisation on Day 1 and neutrophil production on Day 5, despite the presence of estabilshed Listeria infection. The GM−/− mice were unable to control the Listeria infection as well as could their littermate controls, showing a higher bacterial load in the liver on Day 1, and a higher bacterial load in both liver and spleen on Day 5. Thus the GM-CSF deficient mice do constitute a useful model for testing the host response to infection.

EXAMPLE 9

GM-CSF Deficient Mice Are A Suitable Model For Vulnerability To Infection

Blood counts on age-matched 3 week-old GM−/− mice reared under conventional conditions were compared with those from mice reared in a microisolation ("specific pathogen-free"; SPF) environment. The results are summarised in Table 4.

TABLE 4

Comparison between GM−/− Mice Reared in Conventional and SPF Environments

| Parameters | SPF | Conventional | p Value (t test) |
|---|---|---|---|
| Whole body mass (g) | 13.4 ± 0.8 | 11.9 ± 2.1 | NS |
| liver mass (mg) | 576 ± 63 | 576 ± 95 | NS |
| spleen mass absolute (mg) | 72 ± 26 | 95 ± 8 | <0.1 (NS) |
| % body wt | 0.53 ± 0.16 | 0.87 ± 0.16 | <0.02 |
| Haemoglobin g/L | 135 ± 6 | 148 ± 9 | <0.05 |
| Total White Cells x $10^9$/L | 7.7 ± 2.2 | 8.9 ± 3.4 | NS |
| Neutrophil | 0.99 ± 0.70 | 2.98 ± 2.02 | (NS) <0.1 |
| Lymphocytes | 5.55 ± 2.12 | 5.23 ± 1.01 | NS |
| Monocytes | 0.13 ± 0.06 | 0.69 ± 0.50 | <0.05 |
| Eosinophils | 0 ± 0 | 0 ± 0 | NS |
| Platelets x $10^9$/L | 763 ± 91 | 804 ± 16 | NS |

NS = not significant

The mice from the microisolation environment had lower neutrophil and monocyte levels, strongly suggesting that the mice from the conventional environment had been exposed to a range of infectious agents during their first three weeks of life. Despite the lack of statistical significance as assessed by Student T-Tests, there is a marked indication that the mice from the microisolation environment had lower neutrophil levels and a profile suggestive of lesser degree of infection. Thus there is strong evidence for an environmental influence on these parameters.

Discussion

Since the actions of various haematopoietic regulators on target cells appear to overlap, it is possible that individual regulators might be wholly or partially redundant (27). This proposition is most directly assessed by analysis of mice deficient in individual regulators or combinations of regulators. Our analysis of GM-CSF deficient mice up to 3 months of age found that there was no perturbation of major haematopoietic populations in marrow or blood. There are two obvious ways in which to interpret this observation: either GM-CSF may not be a pivotally important regulator of normal haematopoiesis, or alternatively, GM-CSF may contribute to the maintenance of steady-state haematopoiesis, but in its absence other haematopoietic regulators are able to replace the role normally carried out by this regulator. This latter possibility would be further supported if elevated levels of compensatory regulators were demonstrated in the GM-CSF deficient mice. Splenic progenitor cell levels were increased in GM-CSF deficient mice, but this may in part reflect subclinical pulmonary infection in the animals; it will be important to assess to what extent the pulmonary disease process is impacting on "steady-state" haematopoiesis, particularly in the spleen.

The possibility that GM-CSF is a wholly redundant molecule can clearly be discounted in the light of our observation that all GM-CSF deficient mice show abnormal lung development. Our initial studies have not identified the nature of the intrinsic pulmonary defect. However, the same pathology is not seen in control animals, strongly suggesting that it is due to GM-CSF deficiency. A prominent pathological feature is granular eosinophilic intra-alveolar material, which sometimes becomes confluent. This may be a local product, such as pulmonary surfactant phospholipid and protein, either produced in excess or cleared too slowly due to a functional defect of macrophages. The presence of numerous type-C lamellar bodies within alveoli and macrophages is consistent with the accumulation of surfactant components (28). In some areas, the histological appearance of lungs from GM-CSF deficient mice bears a striking resemblance to some forms of alveolar proteinosis, a heterogeneous group of congenital and acquired lung disorders characterised by the intra-alveolar accumulation of surfactant protein, and often complicated by infection (28–31). The roles of GM-CSF or of cells functionally activated by GM-CSF in the production of surfactant by type II alveolar cells and on surfactant clearance have not been studied. Whilst clearance of mucinous secretions in larger airways may also be defective, retained secretions are not prominent in the lungs of younger GM-CSF−/− mice, which already have excessive alveolar material.

A prominent feature of the lung pathology of GM-CSF deficient mice is the presence of infection with a range of opportunistic organisms, including both bacterial and fungal agents. Interestingly, infection of immunocompromised CD4+ T-cell depleted mice with *Pneumocystis carinii* results in peribronchovascular lymphoid hyperplasia of similar appearances to that in GM-/- mice (32), suggesting that the lymphoid hyperplasia may be an aspect of the general pulmonary response to infection. When infection occurs, the host response is usually adequate to prevent death, as only less than 0.5% of GM-/- mice have died from lung infection. However, the lymphoid hyperplasia, prevalent acute bacterial pneumonia, and subclinical multifocal fungal infection suggest that the host response to infection is defective. *Pneumocystis carinii* pneumonia is common in AIDS patients, frequently being the ultimate cause of death.

The presence of large numbers of neutrophils and macrophages within GM-/- lungs indicates that inflammatory cells can still be localized in the lung in the absence of GM-CSF to activate acute and chronic inflammatory processes within tissues, although the numerical and functional adequacy of the cells involved in this response has not been evaluated. Indeed, alveolar macrophages are particularly responsive to GM-CSF, and many cell types present in the lung (including epithelial cells) are capable of GM-CSF synthesis (33,34). It is possible, therefore, that a significant component of the intrinsic pulmonary defect is the absence of local GM-CSF-dependent activation of macrophages involved in either surfactant clearance or infection control. We are testing the influence of environmental factors on the pulmonary manifestations of GM-CSF deficiency by comparing GM-CSF deficient mice raised in conventional and gnotobiotic animal facilities.

The prominent pulmonary pathology accompanying absolute GM-CSF deficiency suggests that GM-CSF may be useful for treatment of lung disorders characterised by accumulation of alveolar material such as alveolar proteinosis, or by infection. Acquired forms of alveolar proteinosis may reflect a local relative deficiency of GM-CSF. Amongst congenital forms of alveolar proteinosis, there may be a human counterpart to murine GM-CSF deficiency for which GM-CSF replacement therapy would be appropriate.

There is considerable evidence that GM-CSF can be effective in treatment or prevention of bacterial and viral infections, and may also have some role in resistance to parasite infection (34–38).

EXAMPLE 10

G-CSF Targeting Vector And Isolation of Targeted ES Cell Clones

The G-CSF targeting vector, illustrated in FIG. 5, was designed to effect a disruption of the G-CSF gene (Tsuchiya, M., Kaziro, Y. and Nagata, S.; Bur. J. Biochem., 1987 165 7–12) comprising a deletion of sequences between the NcoI site in exon 1, which encompasses the translational initiation codon ATG, and the BamHI site 6.3 kb 3' of the BamHI in exon 3. Sequences comprising the *E. coli* lac-z gene with a modification at the 5' end to facilitate cloning into a NcoI site, and the neomycin phosphotransferase gene driven by the phosphoglycerate kinase (PGK) promoter, and with 3' untranslated sequences derived from the vector pMClNeo were inserted at the site of this deletion.

The construct, designated pKOGCSF3b, comprised in the α-hybrid vector backbone derived from the vectors pBR322 and pSP73, from 5' to 3', approximately 1.1 kb of genomic sequence immediately 5' of the G-CSF protein coding sequence, including the G-CSF promoter (the Asp 700 - NcoI fragment), the *E. coli* lac-z and PGK-driven phosphoglycerate kinase neomycin phosphotransferase sequences set out above, and approximately 7 kb of genomic sequence commencing at the BamHI site in exon 3 and limited at the 3' end by a BglII site. This construct is illustrated in FIG. 5b.

In this figure the approximate sizes in kb of genomic sequences are indicated by the bars. The NcoI site labelled with the asterisk encompasses the translation initiation site in exon 1 of the murine G-CSF gene. The BamHI site labelled with a cross lies in exon 3 of this gene. βb represents a 700 bp fragment of the 3' untranslated region and polyA addition motif from the human β-globin gene. The sequences in the neomycin phosphotransferase expression cassette are derived from PGK-Neo (sequences 5' of the NcoI site) and pMC1Neo (sequences 3' of the NcoI site). The Vector backbone is a hybrid of sequences derived from pBR322 and pSp73. The sequences from these two vectors are joined in the targeting construct at the xmnI site in the $Amp^R$ gene to recreate a functional $Amp^R$ gene. The origin of replication is derived from pBR322. The 3' end of the homologous genomic sequence in the construct is defined by a BamHI site in genomic sequences, although this site was ablated during construction of the targeting vector.

Transformation and selection of ES cells were carried out generally as described in Example 1. Polymerase chain reaction was used to screen DNA from each ES cell colony for intergration of the targeting vector by homologous recombination. The PCR primers were as described below Chimeric mice were generated and maintained as described in Example 2. Except where stated, the following observations were obtained using the 5.4 lineage.

EXAMPLE 11

Verification Of G-CSF Gene Disruption

To confirm the structure the targeted allele in G-/- mice, Southern blotting analysis was carried out on genomic DNA from ES cell lines or mouse tail tissues, which was prepared by standard techinques and digested with XbaI. Results are shown in FIG. 6. This figure confirms the predicted structure of the disrupted G-CSF allele, using probes corresponding to sequences both external to and internal to the construct. The probe corresponding to G-CSF genomic sequences lying outside those of the targeting construct pKOGCSF3b was a 5'-SacI-BglII fragment. This probe was diagnostic for homologous integration at one G-CSF allele.

DNA from the ES cell line 5.4, which as described below was confirmed to contain a disrupted G-CSF gene, showed a 14 kb band corresponding to the wild-type allele, as well as a second larger band corresponding to the disrupted allele. The identity of this second band was confirmed by reprobing the Southern blot with a second probe corresponding to 3.2 kb of sequence from the *E. coli* lac-z gene, showing that only a band corresponding in size to that of the disrupted allele contained lac-z sequences. Thus incorporation of these sequences into genomic DNA at the disrupted G-CSF allele was confirmed, as well as the fact that only one copy of the targeting construct sequences was present in the genome of these ES cells.

EXAMPLE 12

PCR Analysis

A PCR probe specific for the disrupted G-CSF allele was used to demonstrate that matings of heterozygous parents resulted in progeny which were homozyous for the disrupted G-CSF allele. These results are shown in FIG. 7. G105 template DNA was shown to have the genotype G+/− by Southern analysis. The symbols −, + and ++ indicate primer concentrations of 0.20 mg/20 µL reaction mixture, and 40 mg/20 µL reaction mixture. The primer sequences are:

```
GL#2    5'-TCC.ATG.ACA.TCT.GTG.GCC.ACC.AGA-3'    SEQ ID NO:3

ES#132  5'-CTG.CAA.GGC.GAT.TAA.GTT.GGG.TAA-3'    SEQ ID NO:4

GL#4    5'-CGG.CCT.CTC.GTC.CTG.ACC.ATA.GTC-3'    SEQ ID NO:5
```

The PCR reaction mixtures were as described in Example 2, except that the concentration of $MgCl_2$ was 2.0 mN and 20 ng of each primer was used, and 35 amplification cycles were performed, with the second being at 62° for 50 second.

When maximal sensitivity was required, PCRS to identify wild-type and disrupted alleles were performed separately. When DNA from tail tissue was screened, PCRs to diagnose wild-type and disrupted allelic status were carried out in a single reaction mixture, which contained 40 mg of primer GL#2 and 20 ng of the other two primers. Primers GL#2 and GL#4 generate a 1.2 kb PCR product from template DNA containing a wild-type allele, while primers GL#2 and ES#132 generate a 1.1 kb PCR product from template DNA containing a disrupted GSF allele.

Results of PCR analysis on the first litter resulting from mating G-CSF +/− parents are shown in FIG. 8. The coat colour pattern demonstrates that progeny homozygous for the disrupted G-CSF allele were produced. This figure also shows PCR Analysis using a probe diagnostic for the disrupted G-CSF allele, confirming that this was the case. We have thus demonstrated germline transmission of the disrupted allele. We have also shown that animals bearing the disrupted allele are viable and fertile.

EXAMPLE 13

Cells From G-CSF Deficient Mice Are Unable To Produce G-CSF

An assay specific for mouse G-CSF was devised and validated. This assay utilised BAF3 cells modified to express receptors for G-CSF. These cells are designated BAF3-GR. Control (untransformed) BAF3 cells, which respond to Multi-CSF and also respond weakly to IL-2, were used as controls. Conditioned medium from thymus, lung, bladder, bone shaft and spleen were compared with a control preparation containing 1 mg/mL of purified G-CSF. These results are shown in FIG. 11, and indicate that the BAF3-GR cells respond specifically to G-CSF, with a lower limit of sensitivity of 30 pg/mL. The results obtained with BAF3 cells show that neither Multi-CSF nor IL-2 in present in the conditioned medium from these organs. The cells were most sensitive to conditioned medium from G+/− lung. Conditioned media from thymus, lung, bladder, bone shaft and spleen were prepared from organs of G-CSF deficient and wild-type animals, and assayed in the BAF3-GR test system. All of the conditioned media from organs of wild-type mice contained titratable levels of bioactive G-CSF, whereas no bioactive G-CSF could be detected in conditioned media from organs of G−/− animals. The results are illustrated in FIG. 12. In addition, assays using sera of G−/−, GM−/− and wild-type mice were unable to detect G-CSF. With serum the lower limit of sensitivity is 120pG/ml

EXAMPLE 14

Haematological Analysis of G-CSF Deficient Mice

Haemoglobin, total leukocyte and platelet estimates were performed on samples from G-CSF deficient mice, as described in Example 6. The results are summarised in Table 5, and show that the G-CSF deficient mice (−/−) have a durable base line neutropaenia compared to wild-type (+/+) or heterozygous (+/−) mice. However, in the G-CSF deficient mice other parameters were within the normal range.

TABLE 5

Haematological parameters in G-CSF −/− Mice

| | Genotype (n) | | |
|---|---|---|---|
| Mice aged 3–4 weeks | G+/+ (31) | G+/+ (30) | G−/− (18) |
| Haemoglobin g/L | 142 ± 12 | 140 ± 13 | 140 ± 15 |
| Platelets × $10^9$/L | 514 ± 222 | 519 ± 199 | 532 ± 198 |
| Total White Cells × $10^9$/L | 6.79 ± 1.66 | 6.25 ± 2.09 | 5.48 ± 2.16 |
| Neutrophils × $10^9$/L | 0.63 ± 0.29 | 0.42 ± 0.27 | 0.17 ± 0.12 |
| Lymphocytes × $10^9$/L | 5.59 ± 1.84 | 5.45 ± 2.05 | 5.04 ± 2.07 |
| Monocytes × $10^9$/L | 0.27 ± 0.19 | 0.22 ± 0.15 | 0.23 ± 0.13 |
| Eosinophils | 0.14 ± 0.12 | 0.13 ± 0.13 | 0.10 ± 0.10 |
| Mice aged 12-16 weeks | G+/+ (5) | G+/− (0) | G−/− (7) |
| Haemoglobin g/L | 169 ± 9 | ND | 169 ± 18 |
| Platelets × $10^9$/L | 798 ± 134 | | 802 ± 125 |
| Total White Cells × $10^9$/L | 10.0 ± 2.5 | | 7.66 ± 3.0 |
| Neutrophils | 0.57 ± 0.19 | | 0.02 ± 0.12 |
| Lymphocytes | 9.10 ± 2.37 | | 7.24 ± 2.94 |
| Monocytes | 0.28 ± 0.19 | | 0.17 ± 0.05 |
| Eosinophils | 0.07 ± 0.08 | | 0.03 ± 0.04 | n = number of mice
Results are expressed as mean ± s.d.

EXAMPLE 16

G-CSF Mice Constitute A Model Of Chronic Neutropaenia

The durability of neutropaenia in the G-CSF deficient mice is evident from the data presented in Example 13. A model of chronic neutropaenia is useful to test new therapies applicable to diseases characterised by chronic neutropaenia, and to test the role of neutrophils in experimental models infection, inflammation or malignancy, in a situation of relative neutrophil deficiency.

For example, α154 day-old female G−/− mouse was killed because it appeared ill, and was found to have a severe endometritis accompanied by enlarged para-aortic lymph nodes, and enlargement of spleen, lungs, heart and liver. Histological examination confirmed pelvic inflammation and endometritis, as well as presence of large numbers of intensively eosinophilic, multinucleated macrophages in the alveoli of the lungs. This mouse had a severely abnormal blood profile (haemoglobin 108 g/L, total leukocyte count 29×$10^9$/L, and platelet count 418×$10^9$/L), and 70% of the circulating leukocytes were monocytes. Endometritis is an unusual infection in mice, and we have not seen it in any other immunocompromised animal in the last twelve months. The infection was probably introduced during mating, and the deficiency of neutrophils and G-CSF probably contributed significantly to the vulnerability of the animal to this infection.

The profound, excessive monocytosis seen in this animal during bacterial infection is very abnormal, and it appears that inability to make G-CSF had impaired its capacity to mount an appropriate granulocytic response to infection. This monocytosis may indicate an attempt to compensate for the lack of neutrophils by generating monocytes and macrophgaes via the remaining intact mechanisms of haemopoiesis.

EXAMPLE 17

G-CSF Deficient Mice Are Vulnerable To Bacterial Infection

G-CSF deficient and wild-type mice were challenged with *Listeria monocytogenes*, administered by intravenous injection at a dose of $5 \times 10^6$ colony forming units per mouse, and haematological and bacterial load end points were examined at 1 hour, 1 day and 5 days after injection. The results are summarised in Tables 6 and 7.

TABLE 6

Haematological Parameters in Mice Injected with Listeria

| | Baseline | | 1 hr Listeria | |
|---|---|---|---|---|
| Haematological | +/+ | G-/- | +/+ | G-/- |
| Parameters | (13) | (13) | (13) | (13) |
| Haemoglobin g/L | 171 ± 8 | 159 ± 8 | 163 ± 9 | 156 ± 6 |
| Platelets × $10^9$/L | 843 ± 122 | 759 ± 118 | 787 ± 149 | 773 ± 126 |
| Total White Cells × $10^9$/L | 9.3 ± 1.7 | 6.0 ± 1.6 | 6.2 ± 1.5 | 3.2 ± 1.0 |
| Neutrophils | 1.05 ± 0.39 | 0.18 ± 0.10 | 2.85 ± 1.39 | 0.30 ± 0.17 |
| Lymphocytes | 7.56 ± 2.12 | 5.62 ± 1.41 | 3.18 ± 0.38 | 2.76 ± 0.99 |
| Monocytes | 0.15 ± 0.09 | 0.14 ± 0.13 | 0.07 ± 0.08 | 0.09 ± 0.08 |
| Eosinophils | 0.04 ± 0.10 | 0.04 ± 0.06 | 0.06 ± 0.06 | 0.04 ± 0.05 |

| | 1 Day Part Listeria Injection | | 5 Days After Listeria | |
|---|---|---|---|---|
| Haematological parameter | +/+ (13) | G-/- (13) | +/+ (8) | G-/- (8) |
| Haemoglobin g/L | 157 ± 8 | 155 ± 4 | 140 ± 11 | 134 ± 8 |
| Platelets × $10^9$/L | 729 ± 134 | 772 ± 143 | 960 ± 251 | 663 ± 464 |
| Total White Cells × $10^9$/L | 10.83 ± 2.97 | 5.20 ± 1.60 | 10.35 ± 1.41 | 3.84 ± 2.05 |
| Neutrophils | 4.28 ± 2.31 | 0.77 ± 0.43 | 2.70 ± 1.26 | 0.33 ± 0.27 |
| Lymphocytes | 5.72 ± 1.80 | 4.16 ± 1.67 | 6.88 ± 2.10 | 3.07 ± 2.22 |
| Monocytes | 0.65 ± 0.32 | 0.23 ± 0.12 | 0.66 ± 0.30 | 0.45 ± 0.39 |
| Eosinophils | 0.17 ± 0.13 | 0.08 ± 0.06 | 0.05 ± 0.08 | 0 ± 0 |
| FACS Phenotype (m) | (8) | (8) | (7) | (7) |
| Antigenic Detected | | | | |
| Mac$^+$ Gr1$^+$ % | 53 | 21 | 42 | 17 |
| Mac$^+$ F4/80$^+$ % | ND | 12 | 19 | |
| Mac$^+$ Gr1$^{low}$ % | ND | ND | 13 | 19 |
| Mac$^+$ Gr$^-$% | 7 | 9 | ND | ND |

Figures in brackets = number of mice
FACS = fluorescence activated cll sorter

TABLE 7

Response of G-/- Mice to Listeria Infection

| | Bacteria Load | | | |
|---|---|---|---|---|
| | Spleen | | Liver | |
| | Bacteria/g | Bacteria/ spleen | Bacteria/g | Bacteria/ liver |
| Wild-type (mouse no.) | | | | |
| 17 | $4.8 \times 10^4$ | $1.1 \times 10^4$ | $9.3 \times 10^4$ | $1.6 \times 10^5$ |
| 18 | $1.1 \times 10^5$ | $3.3 \times 10^4$ | $2.9 \times 10^4$ | $4.3 \times 10^5$ |
| 19 | $5.8 \times 10^5$ | $2.6 \times 10^5$ | $3.9 \times 10^4$ | $6.9 \times 10^4$ |
| 20 | $8.8 \times 10^4$ | $3.7 \times 10^4$ | $3.5 \times 10^4$ | $6.4 \times 10^4$ |
| 24 | $5.6 \times 10^4$ | $2.0 \times 10^4$ | $4.8 \times 10^3$ | $6.1 \times 10^3$ |
| 25 | $2.7 \times 10^5$ | $8.2 \times 10^4$ | $5.2 \times 10^4$ | $5.4 \times 10^4$ |
| 26 | $1.9 \times 10^5$ | $8.0 \times 10^4$ | $1.0 \times 10^5$ | $1.5 \times 10^5$ |
| 23 | $1.1 \times 10^7$ | $2.4 \times 10^6$ | $8.3 \times 10^4$ | $1.0 \times 10^5$ |
| G-/- (mouse no.) | | | | |
| 30 | $1.4 \times 10^5$ | $1.1 \times 10^5$ | $1.4 \times 10^4$ | $2.3 \times 10^4$ |
| 33 | $1.7 \times 10^5$ | $5.4 \times 10^4$ | $8.1 \times 10^4$ | $1.6 \times 10^5$ |
| 37 | $2.0 \times 10^9$ | $3.0 \times 10^8$ | $2.6 \times 10^8$ | $2.8 \times 10^8$ |
| 38 | $4.1 \times 10^8$ | $5.4 \times 10^7$ | $1.3 \times 10^7$ | $1.4 \times 10^7$ |
| 39 | $8.1 \times 10^6$ | $2.4 \times 10^6$ | $3.5 \times 10^5$ | $4.8 \times 10^5$ |
| 36 | $>2.4 \times 10^9$ | $>3.0 \times 10^8$ | $>5.7 \times 10^8$ | $>6.0 \times 10^8$ |
| 32 | $>2.4 \times 10^9$ | $>2.6 \times 10^8$ | $>6.0 \times 10^8$ | $>6.0 \times 10^8$ |

In Table 6 the bacterial counts (raw data) are shown for individual mice, analysed five days after injection of Listeria.

G-CSF deficient mice do not have a readily mobilisable pool of neutrophils, as illustrated by the fact that their neutrophil counts are low 1 hour after Listeria infection compared to wild-type mice. Although their neutrophil levels do increase in absolute terms during the course of Listeria infection, this haematological response is markedly impaired compared to that of the wild-type controls, never attaining even the baseline level of the control group. This impaired haematological response correlates with the generally higher bacterial loads observed in the liver and spleen of these mice 5 days after infection.

EXAMPLE 16

Production of Mice Deficient In Both GM-CSF and CSF-1

GM-CSF deficient mice (genotype GM-/-) and appropriately outbred GM+/+ controls were generated as described above. Initial GM-/-M-/- were generated by interbreeding GM+/-M+/+ and GM+/+M+/- mice (i.e. op/+) and selecting the GM+/-M+/- progeny for interbreeding. These matings generated the various genotypes in appropriate ratios, including GM-/-M-/- and GM+/+M-/- (i.e. op/op). To generate additional GM-/-M-/- animals, GM-/-M+/- mice were mated.

EXAMPLE 17

Viability and Fertility of GM-/-M-/- Mice

From initial matings of GM+/-M+/-×GM+/-M+/- mice, litters of 7±2 pups (n=15) were born. The nine possible genotypes were represented in approximately the expected Mendelian ratios at weaning amongst 144 pups, as summarized in Table 8.

TABLE 8

Ratio of Genotypes in Litters From Matings of Mice
Heterozygous for Both M-CSF and GM-CSF Null Mutations

| Genotype | | Expected ratio | | Observed | |
| --- | --- | --- | --- | --- | --- |
| GM | M | of 16 | of 144 | $n$total | $n$male (%) |
| +/+ | +/+ | 1 | 9 | 10 | 5 (50) |
| +/+ | +/− | 2 | 18 | 16 | 6 (38) |
| +/+ | −/− | 1 | 9 | 10 | 6 (60) |
| +/− | +/+ | 2 | 18 | 19 | 11 (58) |
| +/− | +/− | 4 | 36 | 28 | 16 (57) |
| +/− | −/− | 2 | 18 | 15 | 9 (60) |
| −/− | +/+ | 1 | 9 | 17 | 11 (65) |
| −/− | +/− | 2 | 18 | 21 | 6 (29) |
| −/− | −/− | 1 | 9 | 8 | 6 (75) |

Results from 144 genotyped progeny of 4 double-heterozygous breeding pairs. During this period, the following mice were not genotyped: one litter of 9 pups that dies at 3 days, 2 GM?M−/− males, 2 GM−/−M? males, one GM?M? female.

In particular, GM−/−M−/− mice were not significantly under-represented relative to wild-type mice, indicating that GM−/−M−/− mice were viable and there was no major fetal or neonatal loss, although amongst this genotype, male mice were over-represented. Subsequently, GM−/−M+/−×GM−/−M+/− matings generated litters of which 25/164 (15%) of pups were GM−/−M−/−; this was significantly fewer than expected (p<0.05), and there was again a male preponderance (19/25) (p<0.1). GM−/−M−/− males were fertile; one such male mated with a GM−/−M+/− female has sired 5 litters of 5±3 pups. We have not bred from M−/− females regardless of their GM-CSF status, in view of the difficulties experienced by others.

The Chi-squared test was used to test for differences amongst viability and fertility data. An unpaired t-test was used to test for statistically significant differences in hematological data. Kaplan-Meier survival curves were constructed to compare survival data, and median survivals were tested for difference using the Mantel-Cox statistic. For survival data, mice killed because of apparent illness were regarded as non-survivors. A p-value of ≦0.05 was regarded as statistically significant.

Figure 2C:
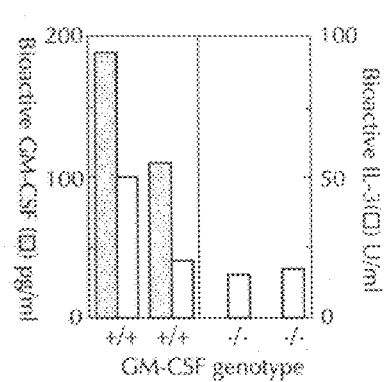

Survival of GM−/−M−/− was compared to that of all other toothless mice (GM+/−M−/− and GM+/+M−/−), and mice deficient only in GM-CSF (GM−/−M+/+) and wild-type (GM+/+M+/+) mice. All toothless (M−/−) mice had significantly reduced survival compared with wild-type and GM-CSF deficient littermates, regardless of whether they were only H-CSF deficient, or both GM- and H-CSF deficient (FIG. 2). Median survivals were: GM+/+M+/+and GM−/−M+/+, not attained with median follow-up for 7 months; M−/−GM+/+ or +/−, 231 days (n=27); GM−/−M−/−, 71 days (n=38). The median ages at death for these two groups of M−/− mice were 33 and 41 days respectively. The median survival of M−/−GM+/+ or +/− mice was significantly shorter than that of GM+/+M+/+ mice (p=0.03), and that of GM−/−M−/− mice was significantly shorter than that of other M−/− mice (p=0.01). Animal husbandary difficulties contributed to the death of most M−/− mice, but at histological examination at histological examination 19/19 GM−/−M−/− mice that died or were killed at ages from 24 days to 324 days because of apparent illness had severe lung disease and acute lobar pneumonia at the time of death; some of the mice killed at ages of 24 to 324 days because of apparent distress were tachypnoeic.

FIG. 18

Phenotypic Features of GM−/−M−/− Mice

GM−/−M−/− mice showed the typical gross phenotypic features of op/op mice ie. osteopetrosis, failure of tooth eruption, and domed head shape. In addition, they all had diseased lungs with many of the features typical of the lung disease observed in GM−/− mice. The GM−/−M−/− mice have age-for-age a more severe and more persistent form of the pathology seen in GM−/−M+/+ mice.

EXAMPLE 19

PCR Diagnosis of GM-CSF and M-CSF Genotype

The allelic status of mice at the GM-CSF locus was determined by PCR as described above. GM-CSF genotypes are designated as follows: wild-type, GM+/+, heterozygous [wild-type/disrupted] GM+/−; and homozygous for the disrupted allele, GM−/−.

Whilst op/op (M-CSF genotype designated M−/−, in parallel to GM-CSF genotypes given above) are readily recognized in litters from M+/−×M+/− matings by their "toothless" phenotype, heterozygous (M+/−) and wild-type (M+/+) littermates are not distinguishable by phenotypic features, and in experiments with op/op (M−/−) it has been typical to use a random selection of M+/− and M+/+ toothed littermates as controls without precise definition of their genotypic status (40,41). In order to eliminate this imprecision and the heterogeneity that a possible gene-dosage effect might introduce, particularly in the face of GM-CSF deficiency, a PCR-based strategy for defining allelic status at the M-CSF locus was devised. By comparison of the murine cDNA sequence (42,43) with the published incomplete genomic structure of the human M-CSF gene (44), it was predicted that the op point mutation (45) lay in an exon homologous to human exon 3. Primers complementary to murine cDNA sequences were used to amplifiy a fragment from murine genomic DNA corresponding to the intron 5' of this exon, and 300 bp of the 3' end of this 1.6 kb PCR-generated fragment sequenced. The diagnostic PCR paired a 5' sense primer from this intronic sequence (5'-TGTGTCCCTTCCTCAGATTACA-3') SEQ ID NO:6 with a 3' antisense primer (5'-GGTCTCATCTATTATGTCTTGTACCAGCCAAAA-3') SEQ ID NO:7 to generate a PCR product of 195 bp or 196 bp dependent on whether or not the thymidine base insertion of the op mutation was present in template DNA. Consequent to a 2 bp mis-match in the 3'-antisense primer (underlined), this PCR product contained a second BglI site dependent on whether template contained the op thymidine insertion. The PCR product was digested with BglI which cut at the intronic BGlI site generating a 96 bp product (confirming restriction enzyme activity in each PCR reaction), and also, in the case of product generated from op template, cut the resulting 100 bp op-template-dependent fragment into diagnostic 70 and 30 bp fragments, but not the 99 bp wild-type-dependent fragment. Heterozygosity (op/+, M+/−) could be distinguished from homozygosity (op/op, M−/−) on the basis of phenotype, but also on the basis of whether the fragment of 100 bp had been completely digested by BglI, or whether uncut 99 bp fragment remained.

Ethidium bromide stained agarose gel of PCR products generated from wild-type, op/op and op/+ genomic DNA, demonstrated the diagnostic 70 bp and 30 bp fragments in BglI digests of PCR products from op-containing template DNA. The latter fragment was visible only in the case of the op/op template.

EXAMPLE 20

Haematological Analysis of GM−/−M−/− Mice

Haemoglobin and platelet levels in mice of the four genotypes mice did not differ significantly at 4–5 weeks of age, but by 18–24 weeks of age, GM−/−M−/− mice had significantly elevated hemoglobin levels. These results are summarized in Table 8. Markedly increased hemoglobin levels were found in some older GM−/−M−/− mice: e.g. one animal that was killed because of apparent distress had a hemoglobin level of 220 g/l.

throughout life: GM−/−M−/− mice of 4–5 weeks of age had granulocyte levels of $3.0 \pm 2.4 \times 10^9/L$ (n=4) compared to $1.3 \pm 0.7 \times 10^9/L$ for age-matched GM+/+M+/+ (n=33) and 3 older mice of age 26, 31 and 47 wks had granulocyte levels of 1.74, 4.37 and $7.7 \times 10^9/l$ respectively. Despite the relative monocytopenia, the diseased lungs of GM−/−M−/− mice contained large numbers of foamy alveolar macrophages, indicating that at least qualitatively monocytes were available for host defence in tissues.

Mice at 4–5 weeks, 18–24 and 28 weeks, were also compared at the results are summarized in Table 9. These results are consistent with those in Table 8.

TABLE 8

Peripheral blood of 18–24 wk GM-CSF and M-CSF deficient mice

| Genotype | | | Hemoglobin | Platelets × | Leukocytes × | Peripheral blood parameter Neutrophils × | Lymphocytes × | Monocytes × | Eosinophils × |
|---|---|---|---|---|---|---|---|---|---|
| GM | M | n | g/l | $10^9/l$ | $10^9/l$ | $10^9/l$ | $10^9/l$ | $10^9/l$ | $10^9/l$ |
| +/+ | +/+ | 4 | 174 ± 4 | 741 ± 138 | 9.3 ± 2.3 | 1.6 ± 0.6 | 7.1 ± 1.6 | 0.21 ± 0.09 | 0.35 ± 0.26 |
| −/− | +/+ | 5 | 174 ± 5 | 929 ± 183 | 8.1 ± 2.3 | 1.3 ± 0.5 | 6.5 ± 1.7 | 0.22 ± 0.11 | 0.12 ± 0.12 |
| +/+ | −/− | 3 | 1742 ± 4 | 823 ± 65 | 6.7 ± 1.4 | 1.2 ± 0.2 | 5.2 ± 1.6 | 0.15 ± 0.06 | 0.08 ± 0.10 |
| −/− | −/− | 7 | 185 ± 10*#Ⓧ | 604 ± 70#Ⓧ | 6.6 ± 1.1* | 2.1 ± 0.9Ⓧ | 4.3 ± 0.9*# | 0.05 ± 0.06*# | 0.07 ± 0.08*#Ⓧ |

\*= p < 0.05 compared to GM+/+M+/+
= p < 0.05 compared to GM−/−M+/+
Ⓧ = p < 0.05 compared to GM+/+M−/−
n = number of mice GM−/−M−/− mice of 18–24 weeks of age had significantly reduced numbers of total leukocytes due primarily to a relative lymphopenia, as has been previously reported for M−/− mice (Table 2 and 2). Monocytes were present in the peripheral blood of GM−/−M−/− mice, but in mice of this age levels were significantly lower than in wild-type and

TABLE 9

Peripheral blood of GM-CSF and M-CSF deficient mice

| Age | Genotype | | | Hemoglobin × | Platelets × | Leukocytes × | Peripheral blood parameter Neutrophils × | Lymphocytes × | Monocytes × | Eosinophils × |
|---|---|---|---|---|---|---|---|---|---|---|
| wks | GM | M | n | g/l | $10^9/l$ | $10^9/l$ | $10^9/l$ | $10^9/l$ | $10^9/l$ | $10^9/l$ |
| 4–5 | +/+ | +/+ | 16 | 134 ± 18 | 771 ± 86 | 6.9 ± 2.8 | 1.3 ± 0.7▽ | 5.6 ± 2.4 | 0.03 ± 0.04 | ND |
|  | −/− | +/+ | 33 | 142 ± 20 | 724 ± 216 | 6.8 ± 2.6 | 1.7 ± 1.5▽ | 5.1 ± 2.0 | 0.07 ± 0.16 | ND |
|  | +/+ | −/− | nil |  |  |  |  |  |  |  |
|  | −/− | −/− | 4 | 147 ± 5 | 474 ± 131 | 5.8 ± 2.7 | 3.0 ± 2.4▽ | 2.7 ± 2.4 | 0.17 ± 0.09 | ND |
| 18–24 | +/+ | +/+ | 4 | 174 ± 4 | 741 ± 138 | 9.3 ± 2.3 | 1.6 ± 0.6 | 7.1 ± 1.6 | 0.21 ± 0.09 | 0.35 ± 0.26 |
|  | −/− | +/+ | 5 | 174 ± 5 | 929 ± 183 | 8.1 ± 2.3 | 1.3 ± 0.5 | 6.5 ± 1.7 | 0.22 ± 0.11 | 0.12 ± 0.12 |
|  | +/+ | −/− | 3 | 1742 ± 4 | 823 ± 65 | 6.7 ± 1.4 | 1.2 ± 0.2 | 5.2 ± 1.6 | 0.15 ± 0.06 | 0.08 ± 0.10 |
|  | −/− | −/− | 7 | 185 ± 10*#Ⓧ | 604 ± 70#Ⓧ | 6.6 ± 1.1* | 2.1 ± 0.9Ⓧ | 4.3 ± 0.9*# | 0.05 ± 0.06*# | 0.07 ± 0.08*#Ⓧ |
|  | −/− | −/− | 2 | 175 | 638 | 5.3 | 3.06▽ | 2.2 | 0.06 |  |

\*= p < 0.05 compared to GM+/+M+/+
= p < 0.05 compared to GM−/−M+/+
Ⓧ = p < 0.05 compared to GM+/+M−/−
▽= total granulocyte count (i.e neutrophils and eosinophils)
ND = not determined GM−/−M+/+ mice and than those in GM+/+M−/− mice (Table 2). GM−/−M−/− had significantly more circulating neutrophils than mice deficient in either factor alone, although not significantly more than their age-matched factor-replete controls. This relative neutrophilia persisted The males of genotype GM−/−, M−/− show features typical of both the CSF-1−/− genotype, such as osteopetrosis and failure of tooth eruption, and of the GM-CSF−/− genotype, such as prepencity to infection, especially pneumonia caused by Gram-negative organisms. These pneumonias are usually fatal. For example, in one group of four GM-/-, M-/- animals, one was found dead at the age of 8 weeks, and pneumonia caused by *Klebsiella oxytoca* was confirmed bacteriologically. Three animals were killed after being found seriously ill; one, killed at six weeks had *Klebsiella oxytoca* pneumonia, one, killed at six weeks had a facial absys caused by a Streptococcus species, and one, killed at twenty weeks had pneumonia caused by *Pasteurella pneumotropica*.

These doubley deficient mice have lung pathology presenting the same features as seen in GM-CSF deficient mice. Despite the deficiency of CSF-1, however, these mice still have monocytes/macrophages at normal or near-normal levels. Thus notwithstanding the double-deficiency these mice are able to maintain steady-state granulopoiesis and monopoiesis.

References cited herein are listed on the following pages, and are incorporated herein by this reference.

The following words used herein are trade marks: Araldite, Epon, Genescreen Plus, Geneticin, Sysmex.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

REFERENCES

1. Gasson J. C. Blood, 1991 77 1131–1145.
2. Metcalf D., Begley C. G., Williamson D. J., Nice B. C., De Larmarter J. D., Mermod J-J., Thatcher D., Schmidt A. Exp. Hematol., 1987 15 1–9.
3. Lang R. A., Metcalf D., Cuthbertson R. A., Lyons I., Stanley E., Kelso A., Kannourakis G., Williamson D. J., Klintworth G. K., Gonda T. J., Dunn A. R. Cell, 1987 51 675–686.
4. Johnson G. R., Gonda T. J., Metcalf D., Hariharan I. K., Cory S. A. EMBO J., 1989 8 441–448.
5. Metcalf D. Science, 1991 254 529–533.
6. Mortensen B. T., Schifter S., Pedersen L. B., Jensen A. N., Hovgaard D., Nissen N. I. Exp. Hematol., 1993 21 1366–1370.
7. Lieschke, G. J., Dunn, A. R. "Physiologic Role of Granulocyte Colony Stimulating Factor: Insights from In Vivo Studies" Molecular Biology of Haematopoiesis, 1992 2 201–216 (Intercept Ltd, Andover, U.K.)
8. Evans, M. J. Mol. Biol. Med., 1989 6 557–565
9. Capecchi, Trends in Genetics, 1989 5 70–76
10. Smithies, O. Trends in Genetics, 1993 9 112–116
11. Koller, B. H. and Smithies, O. Annual Rev. Immunol., 1992 10 705.
12. Corcoran, L. M. Today's Life Science, 1994 6 14–20
13. Miyatake S., Otsuka T., Yokota T., Lee F., Arai K. EMBO J., 1985 4 2561–2568.
14. Stanley E., Metcalf D., Sobieszczuk P., Gough N. M., Dunn A. R. EMBO J., 1985 4 2569–2573.
15. Tybulewicz V. L. J., Crawford C. E., Jackson P. K., Bronson R. T., Mulligan R. C. Cell, 1991 65 1153–1163.
16. Gough N. M., Metcalf D., Gough J., Grail D., Dunn A. R. EMBO J., 1985 4 645–653.
17. Handyside A. H., O'Neil G. T., Jones M., Hooper M. L. Roux's Arch. Dev. Biol., 1989 198 8–55.
18. Mann G. B., Fowler K. J., Gabriel A., Nice E. C., Williams R. L., Dunn A. R. Cell, 1993 73 249–261.
19. Metcalf D. The Hemopoietic Growth Factors (Elsevier, Amsterdam) 1984
20. Kelso A., Gough N. M. Growth Factors, 1989 1 165–177.
21. Metcalf D. Proc. Natl. Acad. Sci. USA, 1991 88 11310–11314.
22. Harlow E., Lane D. Antibodies; a laboratory manual (Cold Spring Harbor Laboratory, NY) 1988
23. Morse H. C., Davidson W. F., Yetter R. A., Coffman R. L. Cell. Immunol., 1982 70 311–320.
24. Yelton D. E., Desaymard C., Scharff M. Hybridoma, 1981 1 5–11.
25. Dialynas D. P., Quan Z. S., Wall K. A., Pierres A., Quintans J, Loken M. R., Pierres M., Fitch F. W. J. Immunol., 1983 131 2445–2451.
26. Ledbetter J. A., Herzenberg L. A. Immunol. Rev., 1989 49 63–90.
27. Metcalf D. Blood, 1993 82 3515–3523.
28. Shelburne J. D., Wisseman C. L., Broda K. R., Roggli V. L., Ingram P. in Diagnostic Electron Microscopy, eds. Trump B. F. & Jones R. T. (John Wiley & Sons, New York), 1983 4 475–532.
29. Rosen S. H., Castleman B., Liebow A. A. N. Engl. J. Med., 1958 258 1123–1142.
30. Nogee L. M., De Mello D. E., Dehner L. P., Colten H. R. N. Engl. J. Med., 1993 328 406–410.
31. Jones C. C. Am. J. Med., 1960 29 713–722.
32. Beck J. M., Warnock M. L., Curtis J. L., Sniezek M. J., Arraj-Peffer S. M., Kaltreider H. B., Shellito J. E. Am. J. Respir. Cell Mol. Biol., 1991 5 186–197.
33. Bilyk N., Holt P. G. J. Exp. Med., 1993 177 1773–1777.
34. Smith S. M., Lee D. K. P., Lacy J., Coleman D. L. Am. J. Respir. Cell Mol. Biol., 1990 2 59–68.
35. Chrane, H. T., Metcalf, D., Cheers, C. Immunology, 1990 71 377–382
36. Frenck, R. W., Sarman, Harper, T. E., Buescher, E. S. J. Infect. Dis., 1990 162 109–114
37. Morrissey, P. J., Charrier, R. J. Immunol., 1990 144 557–561
38. Iida, J., Saiki, L., Ishihara, C., Azuma, vaccine, 1989 7 229–233
39. Freund, M., Kleine, H.-D. Infection, 1992 20 Suppl. 2 S88–S90
40. Marks, S. C., Lane, P. W. J. Heredity, 1976 67 11–18
41. Wiktor-Jedrzejczak, W., Ahmed, A., Szczylik, C., Skelly, R. R. J. Exp. Med., 1982 156 1516–1527
42. Ladner, M. B., Martin, G. A., Noble, J. A., Wittman, V. P., Warren M. K., McGrogan, M., Stanley, E. R. Proc. Natl. Acad. Sci., U.S.A., 1988 85 6706–6710
43. DeLamarter, J. F., Hession, C., Semon, D., Gough, N. M., Rothenbuhler, R., Mermod, J-J. Nuc. Acids Res., 1987 15 2389–90
44. Kawasaki, B. S., Ladner, M. B. In Dexter TM, Garland JM Testa NG eds Colony Stimulating Factors New York: Marcel Dekker 1990 155–176
45. Yoshida, H., Hayashi, S-I., Kunisada, T., Ogawa, M., Nishikawa, S., Okamura, H., Sudo, T., Shultz, L. D., Nishikawa, S-I. Nature, 1990 345 442–444
46. Stanley, E., Leischke, G. J., Grail, D. et al Proc. Natl. Acad. Sci., U.S.A., (in press)
47. Pollard, J. W., Hunt J. S., Wiktor-Jedrzejczak, W., Stanley, E. R. Developmental Biol., 1991 148 273–283

We claim:

1. A method of treatment of alveolar proteinosis comprising the step of administering to a subject an effective amount of GM-SCF, wherein said subject has symptoms of alveolar proteinosis.

2. A method according to claim 1, wherein GM-CSF is administered locally to the lung.

3. A method according to claim 2, wherein the dose of GM-CSF is from 0.1 µg/kg body weight to 20 µg/kg body weight.

4. A method according to claim 1 in which said GM-CSF is administered as an aerosol, via a nebuliser or via an endotracheal tube.

5. A method according to claim 1, wherein the GM-CSF is administered as adjunctive therapy to other treatments.

* * * * *

UNITED STATES PATENT AND TRADEMARK OFFICE
CERTIFICATE OF CORRECTION

PATENT NO. : 6,019,965
DATED : February 1, 2000
INVENTOR(S) : Dunn et al

Page 1 of 2

It is certified that error appears in the above-indentified patent and that said Letters Patent is hereby corrected as shown below:

In column 1, line 23, change "monocyte1/" to read as - - monocyte/ - - .
In column 1, line 25, change "infecting" to read as - - injecting - - .
In column 1, line 27, change "tranagenic" to read as - - transgenic - - .
In column 1, line 38, change "G-CSF" to read as - - GM-CSF - - .
In column 1, line 47, change "i vitro" to read as - - in vitro - - .
In column 4, line 15, change "organisms" to read as - - Organisms - - .
In column 6, line 26, change "Gm-CsF" to read as - - GM-CSF - - .
In column 6, line 41, change "[B2201]" to read as - - [B220] - - .
In column 6, line 56, change "H&B" to read as - - H&E - - .
In column 7, line 56, change "ZL" to read as - - IL - - .
In column 8, line 46, change "51'" to read as - - 5' - - .
In column 9, line 67, change "Bg1 lI" to read as - - BgII - - .

UNITED STATES PATENT AND TRADEMARK OFFICE
CERTIFICATE OF CORRECTION

PATENT NO. : 6,019,965
DATED : February 1, 2000
INVENTOR(S) : Dunn et al

It is certified that error appears in the above-indentified patent and that said Letters Patent is hereby corrected as shown below:

In column 11, line 15, change "0-3343" to read as - - 0-334 - - .
In column 11, line 16, change "0-3133" to read as - - 0-313 - - .
In column 20, line 49, change "α 154" to read as - - a 154 - - .
In column 21, line 30, after "Haematological" insert - - Parameters - - .
In column 21, line 31, delete - - Parameters - -.
In column 21, line 61, col. 3, change "12" to read as - - ND - - .
In column 21, line 61, col. 4, change "19" to read as - - 12 - - .
In column 21, line 61, col. 5, insert - - 19 - -.
In column 22, line 21, col. 2, change "1.4" to read as - - 3.4 - - .
In column 23, line 62, delete the second occurrence of "at histological examination".

Signed and Sealed this

Third Day of April, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 24
      (B) TYPE: nucleotides
      (C) STRANDEDNESS: single
      (D) TOPOLOGY: linear (xi) SEQUENCE DESCRIPTION: SEQ ID NO: 1:

CCAGCCTCAG AGACCCAGGT ATCC                     24

(2) INFORMATION FOR SEQ ID NO: 2:

(i) SEQUENCE CHARACTERISTICS:
      (A) LENGTH: 24
      (B) TYPE: nucleotides
      (C) STRANDEDNESS: single
      (D) TOPOLOGY: linear (xi) SEQUENCE DESCRIPTION: SEQ ID NO: 2:

GTTAGAGACG ACTTCTACCT CTTC                     24

(2) INFORMATION FOR SEQ ID NO: 3:

(i) SEQUENCE CHARACTERISTICS:
      (A) LENGTH: 24
      (B) TYPE: nucleotides
      (C) STRANDEDNESS: single
      (D) TOPOLOGY: linear (xi) SEQUENCE DESCRIPTION: SEQ ID NO: 3:

TCCATGACAT CTGTGGCCAC CAGA                     24

(2) INFORMATION FOR SEQ ID NO: 4:

(i) SEQUENCE CHARACTERISTICS:
      (A) LENGTH: 24
      (B) TYPE: nucleotides
      (C) STRANDEDNESS: single
      (D) TOPOLOGY: linear (xi) SEQUENCE DESCRIPTION: SEQ ID NO: 4:

CTGCAAGGCG ATTAAGTTGG GTAA                     24

(2) INFORMATION FOR SEQ ID NO: 5:

(i) SEQUENCE CHARACTERISTICS:
      (A) LENGTH: 24
      (B) TYPE: nucleotides
      (C) STRANDEDNESS: single
      (D) TOPOLOGY: linear (xi) SEQUENCE DESCRIPTION: SEQ ID NO: 5:

CGGCCTCTCG TCCTGACCAT AGTC                     24

(2) INFORMATION FOR SEQ ID NO: 6:

(i) SEQUENCE CHARACTERISTICS:
      (A) LENGTH: 22
      (B) TYPE: nucleotides
      (C) STRANDEDNESS: single
      (D) TOPOLOGY: linear (xi) SEQUENCE DESCRIPTION: SEQ ID NO: 6:

TGTGTCCCTT CCTCAGATTA CA                                                        22

(2) INFORMATION FOR SEQ ID NO: 7:

(i) SEQUENCE CHARACTERISTICS:
        (A) LENGTH: 33
        (B) TYPE: nucleotides
        (C) STRANDEDNESS: single
        (D) TOPOLOGY: linear (xi) SEQUENCE DESCRIPTION: SEQ ID NO: 7:

GGTCTCATCT ATTATGTCTT GTACCAGCCA AAA                                            33